United States Patent
Skirycz et al.

(10) Patent No.: US 10,976,310 B2
(45) Date of Patent: Apr. 13, 2021

(54) LIGAND IDENTIFICATION BY CO-FRACTIONATION

(71) Applicant: MAX-PLANCK-GESELLSCHAFT ZUR FÖRDERUNG DER WISSENSCHAFTEN E.V., Munich (DE)

(72) Inventors: Aleksandra Skirycz, Potsdam (DE); Sylwia Kierszniowska, Potsdam (DE); Daniel Veyel, Potsdam (DE); Lothar Willmitzer, Kleinmachnow (DE); Monika Chodasiewicz, Potsdam (DE)

(*) Notice: Subject to any disclaimer, the term of this patent is extended or adjusted under 35 U.S.C. 154(b) by 228 days.

(21) Appl. No.: 16/304,182

(22) PCT Filed: May 29, 2017

(86) PCT No.: PCT/EP2017/062841
§ 371 (c)(1),
(2) Date: Nov. 23, 2018

(87) PCT Pub. No.: WO2017/207460
PCT Pub. Date: Dec. 7, 2017

(65) Prior Publication Data
US 2019/0361012 A1    Nov. 28, 2019

(30) Foreign Application Priority Data

May 30, 2016 (EP) .................................. 16172000

(51) Int. Cl.
| | | |
|---|---|---|
| *G01N 33/537* | (2006.01) | |
| *G01N 1/34* | (2006.01) | |
| *G01N 24/08* | (2006.01) | |
| *G01N 33/564* | (2006.01) | |
| *G01N 33/68* | (2006.01) | |

(52) U.S. Cl.
CPC ............. *G01N 33/537* (2013.01); *G01N 1/34* (2013.01); *G01N 24/087* (2013.01); *G01N 24/088* (2013.01); *G01N 33/564* (2013.01); *G01N 33/6845* (2013.01); *G01N 33/6848* (2013.01)

(58) Field of Classification Search
CPC ...... G01N 33/537; G01N 1/34; G01N 24/087; G01N 24/088; G01N 33/564; G01N 33/6845; G01N 33/6848
See application file for complete search history.

(56) References Cited

U.S. PATENT DOCUMENTS

2015/0105280 A1    4/2015  Regnier et al.

FOREIGN PATENT DOCUMENTS

| EP | 0080109 A1 | 6/1983 |
| WO | 2004019967 A1 | 3/2004 |
| WO | 2006015796 A1 | 2/2006 |
| WO | 2014082083 A1 | 5/2014 |

OTHER PUBLICATIONS

Ozer et al. (Molecular Therapy—Nucleic Acids 2014 3: e183). (Year: 2014).*
Schutze et al. Probing the SELEX Process with Next-Generation Sequencing PloS One 2011 6: e29604. (Year: 2011).*
Yang et al. Strategies of the Discovery of Therapeutic Aptamers Expert Opin. Drug Discov. 2011 6:75-78 (Year: 2011).*
Kaewkhomdee et al. (Anal. Bioanal. Chem. 2010 396:1355-1364), (Year: 2010).*
Manaskova-Postlerova et al. (J. Chromatography B 2011 879:100-106) (Year: 2011).*
Matczuk et al. (Analyst 2015 140:3492-3499) (Year: 2015).*
Bao et al. (Analytical Chem. 2014 86: 10016-10020) (Year: 2014).*
Strizak et al. (Science of Total Environment 470-471 (2014) 159-170) (Year: 2014).*
Stephen Quirk Triggered release of small molecules from proteinoid microspheres Journal of Biomedical Materials Research. Part A, vol. 91A, No. 2, Nov. 1, 2009 (Nov. 1, 2009), pp. 391-399 ISSN:1549-3296, DOI:10.1002/jbm.a.32241.

* cited by examiner

*Primary Examiner* — Changhwa J Cheu
(74) *Attorney, Agent, or Firm* — Perdue IP Law, APC; Donna O. Perdue

(57) ABSTRACT

This invention relates to a method of determining ligands of macromolecules, said method comprising or consisting of (a) subjecting a sample comprising (i) complexes formed by said macromolecules and said ligands and (ii) unbound ligands to a method which separates said complexes from said unbound ligands; (b) releasing ligands from complexes obtained in step (a); and (c) subjecting the released ligands obtained in step (b) to a chemical analysis method, thereby determining said ligands of said macromolecules.

20 Claims, 14 Drawing Sheets

A

B

LIGAND IDENTIFICATION BY CO-FRACTIONATION

CROSS-REFERENCE TO RELATED APPLICATIONS

Figure 1:
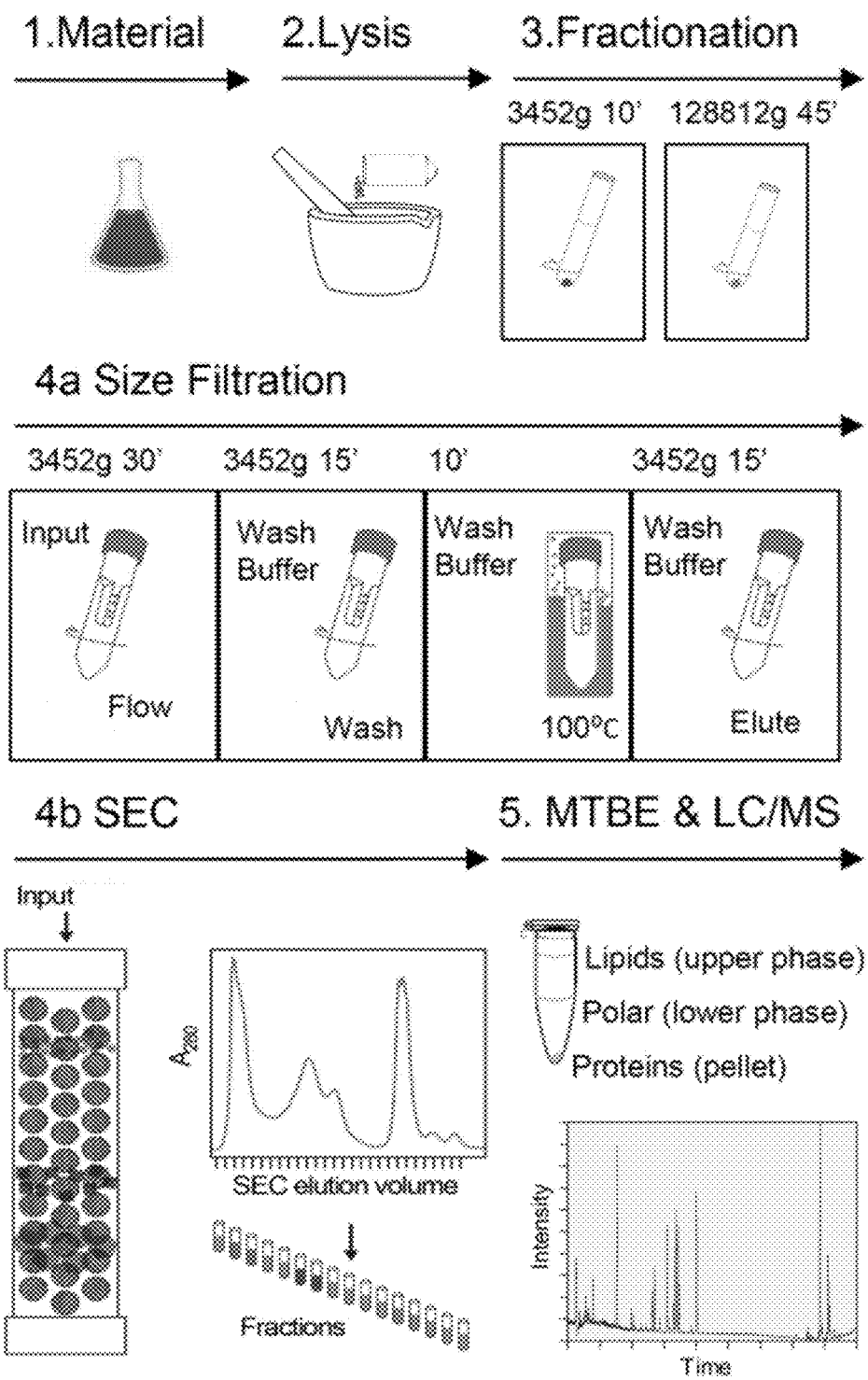

This application is a national stage application under 35 U.S.C. § 371, of International Application No. PCT/EP2017/062841, filed May 29, 2017, which claims benefit of priority to European Application No. 16172000.8, filed May 30, 2016, each of which is incorporated herein by reference in its entirety.

This invention relates to a method of determining ligands of macromolecules, said method comprising or consisting of (a) subjecting a sample comprising (i) complexes formed by said macromolecules and said ligands and (ii) unbound ligands to a method which separates said complexes from said unbound ligands; (b) releasing ligands from complexes obtained in step (a); and (c) subjecting the released ligands obtained in step (b) to a chemical analysis method, thereby determining said ligands of said macromolecules.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Recent years brought significant advances in so called "omics" techniques allowing for simultaneous quantification of thousands of biological molecules including transcripts, proteins and metabolites (Joyce & Palsson, *Nat. Rev. Mol. Cell Biol.* 7, 198-210 (2006)). These molecules present building blocks of life but it is their interactions that enable life. Large-scale analysis of molecular complexes is thus one of the next great challenges to be addressed. Among these, the analysis of protein-metabolite interactomes (PMI) is particularly troublesome considering the large diversity of small molecules, in particular their detection, identification, and immobilization when used as bait. Nevertheless, the importance of PMIs, for both academic research and drug discovery, has driven the development of methods for PMI analysis (Li et al., *Cell* 143, 639-50 (2010); Savitski et al., *Science* 346, 1255784 (2014)). Generally, existing approaches include those using small molecule as bait to "fish out" interacting proteins (Maeda et al., *Nat. Protoc.* 9, 2256-66 (2014)) or vice versa (Hulce et al., *Nat. Methods* 10, 259-264 (2013); Reinhard et al., *Nat. Methods* 12, 1129-1131 (2015)). Such assays provide an effective way to characterize protein-metabolite complexes when at least one of the interacting partners is known. However, they are limited in that they only allow one to one interactions to be detected.

Bioactive compounds (including drugs) are small molecules which exert a desired function in a given biological system by modulating the state of the system into a desired direction. They represent the key ingredients in both pharmaceutical, agrochemical and bioengineering industries (life science industry) with their turnover exceeding 1 trillion Euro annually.

In order to develop new drugs for the life science market, numerous hurdles both in the development and market entry phase and the early discovery phase need to be overcome.

As to the discovery phase, leads for new small molecule based drugs are obtained following one of the two principal routes: (1) Numerous small molecules are applied to a given biological system and the response of the system/its phenotype is monitored. Small molecules inducing the desired response/phenotype are chemically optimized and their molecular target in the biological system elucidated. (2) A macromolecular target (in most cases a protein or an RNA) is identified which needs to be modulated in order to reach the desired response of the system/phenotype. In case of the second approach a key challenge lies in the identification of small molecules influencing the activity of the target macromolecule in the desired way. To this end comprehensive (chemical) libraries of up to several millions of diverse compounds are screened for their ability to modulate the activity of the target using high throughput screens (HTS).

This process of identifying a compound which has the ability to modulate the activity of the macromolecular target and thus serves as a lead compound to develop the ultimate drug suffers from two shortcomings.

(1) As a rule, compounds exogenous to the biological system under study are applied. Examples are compound libraries consisting of millions of chemically synthesized compounds or natural compound (libraries) which are in most cases derived from different biological systems (e.g. plants or microorganisms). Target organisms in the pharmaceutical industry, on the contrary are humans respectively animals (mostly mammals) in the veterinary industry. A reason for this minor use of endogenous compounds as lead compounds is the very limited knowledge about endogenous compounds present in human systems which regulate the activity of macromolecular entities such as proteins, RNA and the like.

(2) As described above, HTS have been developed which allow the screening of several millions of compounds with respect to their ability to modulate the activity of a given target macromolecule (protein, RNA). Despite its high-throughput nature, this process is time consuming and as a rule done by testing one compound after the other in discrete assays. Only recently, novel approaches have been introduced which allow the testing of mixtures of compounds. An exemplary procedure, which relies on the addition of DNA tags to the chemical compound (see, e.g. Mullard, Nature 530, 367-369 (2016), proves to be of major advantage however it suffers from two inherent problems: (i) it is only applicable to chemically synthesized compound libraries; and (ii) the addition of the DNA tag leads to a change in the structure of the compound thus leading to false negatives and false positives during the screening. With respect to the first limitation, this means that natural compounds which have the highest hit rate in screenings are excluded.

In view of the shortcomings of the prior art, the technical problem underlying the present invention can be seen in the provision of improved or alternative means and methods for elucidating intermolecular interactions in biological systems or identifying modulators of biological macromolecules.

The present invention, in a first aspect, relates to a method of determining ligands of macromolecules, said method comprising or consisting of (a) subjecting a sample comprising (i) complexes formed by said macromolecules and said ligands and (ii) unbound ligands to a method which separates said complexes from said unbound ligands; (b) releasing ligands from complexes obtained in step (a); and (c) subjecting the released ligands obtained in step (b) to a chemical analysis method, thereby determining said ligands of said macromolecules.

The term "ligand" in accordance with the invention designates a molecule which is capable of binding to a macromolecule of the invention, macromolecules being defined further below. Binding of ligands to macromolecules is direct in the sense that a chemical and/or physico-chemical interaction between ligand and macromolecule occurs. Said chemical and physico-chemical interactions are preferably selected from dipole-dipole interactions, dipole-charge interactions, charge-charge interactions, van-der-Waals interactions, hydrophobic interactions, stacking interactions and covalent interactions. Generally speaking, the interaction between ligand and macromolecule may be covalent or non-covalent. Preference is given to non-covalent interactions.

Generally speaking, but not necessarily, a ligand is smaller, preferably at least an order of magnitude smaller, than a macromolecule in terms of its molecular mass.

Ligands may be cognate ligands. The term "cognate ligand" designates a ligand which interacts under physiological or in vivo conditions with a macromolecule, the ligand generally being formed by the biosynthetic machinery of the given biological system. Ligands in accordance with the invention may be cognate ligands, but do not have to be so. For example, a xenobiotic compound, i.e. a compound which does not occur in nature, especially not in an in vivo setting, may be found to be a ligand of a macromolecule.

It is, however, expected that endogenous compounds, i.e. cognate ligands, have a number of advantages such as lower toxicology and higher specificity as they are the result of evolutionary selection within the biological system under study.

In terms of binding strength, it is preferred that the dissociation constant $K_D$ of the ligand-macromolecule complex is in or below the two digit micromolar range, i.e. less than 100 µM. Preferably, $K_D$ is less than 10 µM, less than 1 µM, less than 100 nM, less than 10 nM, less than 1 nM, less than 100 pM, or less than 10 pM.

The term "unbound ligand" refers to ligands which are not bound to macromolecules. The term comprises molecules which are not capable of binding to any macromolecule present in the sample subjected to the method in accordance with the first aspect. Furthermore, the term, in its broadest sense, extends to those molecules which are capable of binding a macromolecule, but do not occur in bound form, for example for thermodynamic reasons such as presence of the respective ligand in excess.

In a preferred embodiment, the term "unbound ligand" designates only those molecules which are not capable of binding any macromolecule present in the sample, regardless of the amounts of macromolecules and ligand. These are molecules, generally smaller than macromolecules (as noted above), which do not interact with macromolecules comprised in the sample.

A macromolecule in accordance with the invention is a molecule which is greater than the above defined ligand in terms of its molecule mass. In general, the macromolecule is significantly larger than the ligand, preferably by one, two or more orders of magnitude. The term "order of magnitude" corresponds to a factor 10. Preference is given to biological macromolecules. Biological macromolecules are large molecules as they occur in biological systems. Biological macromolecules are generally polymers or polycondensates of smaller building blocks. A particularly preferred type of macromolecule is a polypeptide. Also preferred are nucleic acids. Nucleic acids include both DNA and RNA, RNA being preferred.

In a strict sense, the term "macromolecule" designates a single molecule. In a wider sense, also more complex molecular architectures are embraced by the term "macromolecule". Examples of more complex architectures include those molecules or molecular assemblies where more than one polymer or polycondensate are bound to each other. The manner in which two or more polymers or polycondensates are connected to each other may be covalent and/or non-covalent. An example of a covalent molecular assembly which also falls under the term "macromolecule" in accordance with the present invention is insulin. As is known in the art, insulin comprises two polypeptide chains which are linked by disulfide bridges. An example of a non-covalent molecular assembly which also meets the requirements of the term "macromolecule" in accordance with the present invention is hemoglobin which is an $\alpha_2\beta_2$ non-covalent heterotetramer. Accordingly, it is understood that the term "macromolecule" includes dimers, trimers, tetramers, pentamers, hexamers, and higher order oligomers of polymers or polycondensates which are either identical to each other or different from each other, thereby giving rise to homooligomers or heterooligomers, respectively. Also in this particular context, preference is given to those polycondensates which are polypeptides.

The term "macromolecule" also extends to organelles, especially to those organelles which are sometimes referred to as "minor organelles". Minor organelles include proteasomes and ribosomes. Accordingly, it is understood that the term "macromolecule" extends to those macromolecular assemblies which comprise both polypeptides and nucleic acids (in the case of the ribosome RNA). The term also includes major organelles such as mitochondria and chloroplasts.

It should be noted that ligand and macromolecule may be of the same compound class however preferably they differ in molecular weight by at least a factor of at least 10, at least 20, at least 30, at least 40, at least 50, more preferably at least 100. For example, the ligand may be a peptide and the macromolecule a polypeptide. Having said that, it is also envisaged to investigate ligand-macromolecule interactions where ligand and macromolecule are exclusively of different molecular architecture. This would apply to a scenario where small organic molecule ligands which are not peptidic in nature are investigated for their binding capability to a proteinaceous macromolecule.

The term "sample" is not particularly limited. Preferred embodiments, which are described in more detail below, include cell-free cell extracts. Owing to the definition of the term "macromolecule" as given above, the sample does not have to be a clear liquid, but may be so. Also, it may be a suspension of macromolecular assemblies and/or organelles.

Said sample may comprise, in addition to complexes and ligands, ligand-free macromolecules, also referred to as unbound macromolecules.

We note that the method in accordance with the first aspect, in its broadest definition, does not require the bringing into contact of macromolecules with ligands. In fact, said sample may originate from cells, tissue, or organisms. In these biological systems generally there is presence of both macromolecules and ligands, ligands including or being confined to cognate ligands of macromolecules present in the sample. Accordingly, it is understood that in a preferred embodiment, any step of bringing macromolecules into contact with ligands is excluded.

Having said that, it is not excluded that macromolecules and candidate ligands are deliberately brought together prior to subjecting them to the method in accordance with the first aspect.

Step (a) of the method of the first aspect defines an analytical method. Step (a) may be, but does not have to be performed in columns. Preferred methods in accordance with step (a) are described below. Importantly, the method of step (a) provides for separating unbound ligands from bound ligands, bound ligands being present in the form of the recited complexes.

Generally, but not necessarily, ligands on the one hand have a small molecular weight as compared to both complexes and unbound macromolecules. As such, step (a) may yield, upon removal of said ligands, a mixture of complexes and unbound macromolecules, to the extent the latter are present.

Once unbound ligands are separated from complexes, the method of the invention in accordance with the first aspect proceeds to releasing ligands from macromolecules.

Given that unbound ligands were already removed in step (a), it follows that the mixture obtained in step (b) contains only those ligands which initially were present in the form of complexes, i.e. bound to macromolecules.

Step (c) of the method of the first aspect provides for determining said ligands. Preferred methods of chemical analysis are disclosed below. Especially preferred is mass spectrometry (MS).

The method in accordance with the first aspect is neither limited to a single ligand or a small number of ligands, nor is it limited to a single macromolecule or a small number of macromolecules. To the contrary, complex ligand-macromolecule interaction networks such as protein-metabolite interactomes (PMIs) can be conveniently elucidated and mapped with the method of the first aspect. Deviant from the prior art, and quite surprisingly, this is done without the need for specific protein baits or ligand baits.

The invention exploits the observation that small molecules, to the extent they are ligands of macromolecules, co-elute with the macromolecule when separated according to size. To this end, conditions for step (a) of the method of the invention are chosen such that said complexes remain stable. Stability will generally be given for the preferred dissociation constant values given above. Suitable conditions include aqueous solutions such as buffered aqueous solutions.

The method according to the first aspect of the invention, in its broadest definition, does not require the determining of the recited macromolecules. Yet, the method confers distinct advantages. For example, and to the extent ligands are used which are test compounds, i.e. compounds the binding properties of which may be unknown such as xenobiotic compounds, the method in accordance with the first aspect provides information about which type of compounds binds to macromolecules. "Type of compound" in that context refers to properties such as chemical structure, presence of functional groups, log P value and the like. In other words, the method in accordance with the first aspect provides for defining a subspace in chemical space, wherein said subspace is characterized in that it contains those test compounds which are more likely to be ligands of macromolecules. This is valuable information for the design of libraries of test compounds, such libraries e.g. being tailored for certain types of biological macromolecules or biological macromolecules in general.

In a preferred embodiment, said ligands (i) are ligands which occur naturally in a biological system such as metabolites, peptides, lipids and nucleic acids including small RNAs and oligonucleotides; (ii) are test compounds; (iii) have a molecular mass between about 50 Da and 2000 Da; and/or (iv) are small organic molecules.

Exemplary metabolites include glycylproline, FAD, cAMP, riboflavin, FMN and NAD. "cAMP" includes 2',3' cAMP and 3',5' cAMP. Example 8 illustrates the use of the present invention for identifying 2',3' cAMP as a ligand of a biological macromolecule.

Small RNAs in accordance with item (i) include microRNAs and small interfering RNAs (siRNAs). Typical siRNA molecules are described in WO02/44321 and references cited therein.

The term "test compound" in accordance with the invention is a functional designation. It means that, prior to performing the method of the invention, it is not known whether said compound binds to any macromolecule. A test compound may be of synthetic origin. It may be a xenobiotic compound, but does not have to be. Accordingly, the method in accordance with the first aspect can be used for screening purposes, in particular for the identification of previously unknown ligands.

A preferred molecule weight range in accordance with item (iii) of this preferred embodiment is between 100 Da and 1000 Da.

The term "small organic molecule" has its art-established meaning and refers to molecules comprising carbon atoms and furthermore one or more of the following atoms: hydrogen, oxygen, nitrogen, sulphur, phosphorus and halogens such as F, Cl and Br. "Small" designates molecular masses in accordance with item (iii).

In a further preferred embodiment, said biological system is a cell, a tissue, an organism, a sample taken from an organism, a composition secreted by an organism, or an environmental sample. The mentioned samples are also preferred samples in accordance with step (a) of the method of the first aspect of the invention. Preferably, said biological system is the source the sample originates from.

Preferably, said cell is an isolated cell, an in vitro cell, an ex vivo cell or a cell in culture.

Preferably, said tissue is an ex vivo tissue, a tissue sample previously taken from an organism or an artificial tissue.

Said organism may be a mammal including human. It may also be a non-human organism.

Having said that, it is understood that the recited biological system as such is not being processed by the method of the invention. Rather, the biological system is used to define a preferred category of ligands in the sense that said preferred category of ligands are those ligands which originate from biological systems.

Preferably, said environmental sample is a sample comprising biological material such as a sample from a stretch of water comprising organisms living therein or a soil sample comprising organisms living therein.

In a preferred embodiment, a ligand determined in step (c) is a candidate lead compound for developing a modulator, e.g. inhibitor or activator, of a macromolecule.

As known in the art, especially in the field of pharmacology, a molecule, once known to be capable of binding to a macromolecule which is considered as a therapeutic target molecule, can be developed or optimized in order to eventually yield a medicament. The starting compound for such process of development or optimization is also referred to as lead compound.

In a preferred embodiment, when using test compounds, a ligand determined in step (c) is a test compound capable of binding to one or more of said macromolecules.

As noted above, in a preferred embodiment, the method of the first aspect can be used for screening purposes, namely to identify, among test compounds, those which are capable of binding to a macromolecule. Those which are capable of binding are termed "ligand" in accordance with the present invention.

In a further preferred embodiment, said macromolecules are (1) proteins, nucleic acids, membranes and/or macromolecular assemblies such as organelles; and/or (2) (i) a proteome or RNAome; (ii) comprised in a cell extract, said cell extract preferably being a cell lysate; or (iii) proteins encoded by a library of nucleic acids or nucleic acids, preferably RNAs, encoded by a library of nucleic acids.

Preferably, said cell lysate is cell-free. E.g., it has been subjected to centrifugation to remove insoluble material. Preferably, it has been subjected to no further purification.

The term "protein" includes polypeptides, but is not confined thereto. A polypeptide is a single continuous chain of amino acids. Proteins may have more complex structures such as homo- or heterooligomers of the same or different polypeptides (for details see further above). In terms of constituent monomeric building blocks, preference is given to the 20 proteinogenic α-amino acids. Having said that, also other α-amino acids such as 2-amino-butyric acid, pyrrolysine or selenocysteine may be present. Instead of α-amino acids, one or more β-amino acids and/or D-amino acids may be present.

Amino acids may be derivatized. This may either be in the form of the naturally occurring post-translational modifications such as phosphorylation or glycosylation, or may be artificially achieved in synthetically prepared amino acids or polypeptides. Examples of the latter include O-methylserine. The C-terminus of a polypeptide chain may be esterified, e.g. with $C_1$ to $C_4$ alkanols and/or the N-terminus amidated, e.g. with $C_1$ to $C_4$ primary alkanamines.

The term "nucleic acid" includes DNA and RNA. The term "nucleic acid" also extends to molecules with a backbone which is not the canonical sugar-phosphate backbone. Examples are peptide nucleic acids (PNAs). In the nucleic acids, the nucleobases may be modified. Also the sugar may be modified, especially in ribonucleotides, for example at the 2'-position, e.g. with O-methyl or fluoro. Also locked nucleotides (LNAs) may be used.

As mentioned above, the term "macromolecule" includes macromolecular assemblies. These in turn may comprise one or more of proteins, nucleic acids and lipids. The mentioned membranes may be closed vesicles. Membranes and vesicles may comprise one or more proteins, in particular transmembrane and/or membrane associated proteins.

The term "proteome" has its art-established meaning and refers to the complete set of expressed proteins in a given organelle, cell, cell type, tissue or organism. As such, quite complex mixtures may be analyzed and complex interaction networks can be elucidated with the method of the present invention. Complete proteomes have already been analyzed and this is shown in the examples enclosed herewith.

Similarly, the term "RNAome" has its art-established meaning and refers to the complete set of RNA in a given cell, cell type, tissue or organism.

Related to the above, complex samples may be conveniently analyzed. An example of a complex sample is a cell extract. The cell extract may be obtained by breaking up cells and merely removing insoluble material, e.g. by centrifugation, and thereafter subjecting the remaining cell free cellular extract, preferably directly, to analysis with the method of the first aspect. This is convenient because any further purification is generally dispensable. This is advantageous because any bias or loss of material which could be caused by additional steps is avoided. It is surprising that the method in accordance with the first aspect can conveniently and successfully handle such rather crude and complex samples.

In an alternative to analyzing naturally occurring mixtures of proteins such as proteomes, the macromolecules may be proteins which have been synthesized using heterologous systems or chemical synthesis, for example proteins encoded by a library of nucleic acids and expressed in a suitable microorganism.

In a preferred embodiment, (i) said fractions cover a molecular mass range from about 10 kDa to about 10000 kDa; and/or (ii) 2, 3, 4, 5, 6, 7, 8, 9, 10 or more fractions are collected.

This preferred embodiment requires that said method yields fractions. This can be the result of a size cut-off, or the separating properties of the compounds comprised in the sample in accordance with step (a), especially the separating properties of ligands, macromolecules and complexes formed by ligands and macromolecules, are a continuous function of their size and/or charge.

If not indicated otherwise, it is understood that macromolecules, when not comprised in a complex, are ligand-free.

Generally speaking, the molecular mass range is preferably adjusted to the type of application. When entire proteomes, especially unknown or partially unknown proteomes are to be characterized with regard to their interaction partners, the recited range from 10 kDa to 10000 kDa is a useful starting point. Other preferred ranges are from 10 kDa to 1000 kDa and from 10 kDa to 600 kDa.

As regards the number of fractions, the attention is also directed to the examples enclosed herewith. To the extent 10 to 50, for example 15, 20, 25, 30, 35, 40 or 45 fractions are collected, comprehensive elution profiles of ligands may be obtained. As regards the term "elution profile", we refer to the preferred embodiment disclosed below.

To the extent a plurality of fractions are subjected to releasing in step (b), and the amount of a given ligand is determined for each of said fractions, an elution profile of said given ligand is obtained. An elution profile is a data set which may be shown as vector, table or as a two-dimensional diagram where the amount of ligands is presented in dependency of the separation property of the complexes comprised in the sample being analyzed, the separation property preferably being size. Elution profiles are described in the examples and shown in the figures. The observation of multimodal distributions in elution profiles is generally indicative of a plurality of macromolecules binding to a given ligand. The terms "elution profile" and "fractionation profile" are used equivalently herein.

In a further preferred embodiment, one or more macromolecules are determined by a chemical analysis method as described herein, in particular MS, proteomic analysis, NMR spectrometry, sequencing (nucleic acid and/or protein sequencing) or detection by antibodies. In more detail and referring to macromolecules which are proteins, identification can be done on digested proteins with MS coupled to LC or MALDI, or on intact proteins with a suitable mass spectrometry instrument or other protein identification methods like detection by antibodies, NMR or protein sequencing. For example, after cleavage of proteins with specific proteases or unspecific chemicals, they are preferentially subjected to MS/MS analysis for either (i) de novo sequencing in case of modified proteins or proteomes from organisms whose genome is not sequenced, or (ii) identification by search against the available databases.

Determining macromolecules preferably includes determining both macromolecules which were bound to a ligand and macromolecules which were not bound to a ligand.

Once a macromolecule binds a ligand, the macromolecule and the ligand will co-elute or co-fractionate, these two terms being used equivalently herein. By analyzing the co-fractionation or co-elution behavior, it is determined which ligand binds to which macromolecule. Statistical methods may be used for that purpose.

"Determining" as used herein refers to elucidating chemical structure and/or composition and may include quantitation.

In a particularly preferred embodiment, it is determined which ligand binds which macromolecule, preferably by determining the amount of a given macromolecule in each of the fractions in accordance with the invention and comparing fractionation profiles or elution profiles of ligands with such obtained fractionation profiles or elution profiles of macromolecules.

This preferred embodiment provides for the elucidation of one or more macromolecule-ligand interactions in the sense that the identity of the interacting molecules is determined.

In other words, the present invention provides a method of determining complexes between ligands and macromolecules, said method comprising or consisting of (a) subjecting a sample comprising (i) complexes formed by said macromolecules and said ligands and (ii) unbound ligands to a method which separates said complexes from said unbound ligands; (b) releasing ligands from complexes obtained in step (a); (c) subjecting the released ligands obtained in step (b) to a chemical analysis method, thereby determining said ligands of said macromolecules, (d) determining one or more macromolecules by a chemical analysis method and (e) determining which ligand binds which macromolecule.

In a complex mixture of macromolecules, for example a cellular lysate, certain macromolecules may closely co-elute along several fractions in a given separation method, for example SEC, due to similar hydrodynamic volume of the macromolecular complexes. The most likely macromolecular interaction partner of a released small molecule of a particular fraction in step (c) is the one having the most similar elution profile to the ligand.

To find similar elution profiles for each respective ligand among said macromolecules, the elution profiles can be visually compared. Preferably, they are subjected to mathematical analysis, more specifically statistical analysis, preferably after appropriate and art-established transformation of the data, like scaling and/or centering. Mathematical analysis of elution profiles generally embraces identifying causal relationships with correlation or similar profiles by applying various distance measures between vectors representing elution profiles, like Euclidean distance, Manhattan distance and the like. The results of such co-elution (or co-fractionation) analysis maybe displayed as lists, two dimensional diagrams, or networks (see FIG. 4). The macromolecule having the highest correlation coefficient or smallest distance to a particular ligand represents the most likely interaction partner.

The above disclosed preferred embodiment, namely the determination of which ligand binds which macromolecule directly provides information about which macromolecule in said sample was originally bound to a ligand. In other words, a distinction is provided between unbound macromolecules, if present, and macromolecules which, at the outset of the method of the invention, were bound to ligands. Those macromolecules which were bound to ligands, preferably low molecular weight ligands, i.e. ligands which have a molecular weight of less or equal one tenth of the molecular weight of the respective macromolecule, are macromolecules which have an elevated probability of being druggable. "Elevated" in this context means a statistically significant difference when compared to all macromolecules present in a given sample. To explain further, a key question in developing drugs for a macromolecule such as a protein is the question of "druggability" of the target, i.e. its general accessibility to modulation of its activity by a small molecule. By determining one, more or all macromolecule-ligand complexes present in a given biological system, those macromolecules will be identified which are druggable, thus facilitating the further development and selection of druggable targets.

As a consequence, the present invention also provides a method of identifying druggable macromolecules, said method comprising or consisting of (a) subjecting a sample comprising (i) complexes formed by said macromolecules and their ligands and (ii) unbound ligands to a method which separates said complexes from said unbound ligands; (b) releasing ligands from complexes obtained in step (a); (c) subjecting the released ligands obtained in step (b) to a chemical analysis method, thereby determining said ligands of said macromolecules, (d) determining one or more macromolecules by a chemical analysis method and (e) determining which ligand binds which macromolecule, wherein a macromolecule binding a ligand is a druggable macromolecule.

The ligands recited in the above disclosed method of identifying druggable macromolecules are preferably cognate ligands. In other words, they are ligands as they occur in nature. Accordingly, and similar to the methods disclosed further above, it is a preferred embodiment of the method of identifying druggable molecules, that any step of bringing macromolecules in contact with ligands is excluded. In fact, such bringing into contact is considered dispensable when naturally occurring macromolecule-ligand interactions are to be investigated.

The above disclosed analysis of co-elution behavior may be extended. Such more complex methods will generally involve one or more further analytical methods in addition to a given analytical method in accordance with step (a) of the main embodiment. In other words, the methods of the invention, in accordance with this preferred embodiment, may comprise at least 2, at least 3, at least 4, at least 5, at least 10, at least 15, or at least 20 different separation methods, preferably chromatographic separation methods.

More specifically, possible implementations of this preferred embodiment include repeatedly performing the method in accordance with the first embodiment, wherein for each repetition a different chromatographic method and/or different chromatographic material is used. Preferred chromatographic methods and materials are detailed further below.

Alternatively or in addition, step (a) of the method of the main embodiment of the present invention may be implemented such that at least 2, at least 3, at least 4, at least 5, at least 10, at least 15, or at least 20 different separation methods are comprised. In that case, and deviant from the above described implementation, this does not amount to parallel performing of different chromatographies, but subsequent performing of different chromatographies, wherein the result of a first chromatography is fed into a second chromatography. As sated above, the two approaches may be combined.

The use of more than one separation using different separation principles and/or different chromatographic resins and then determining the co-elution behavior over more than one separation approach reduces the number of potential candidates for macromolecule-ligand pars. Preferred approaches use at least 2 and up to 20 different chromatographic separations and use statistical analysis of the elution behavior of macromolecules and ligands to determine the most likely macromolecule-ligand complexes.

The above disclosed preferred embodiment is considered to be particularly suitable in those instances where very complex mixtures are to be analyzed. Particularly complex mixtures may render the determining of which ligand binds which macromolecule difficult.

Under such circumstances, in addition or as an alternative to the above preferred embodiment, more than one sample may be analyzed. Such different samples may be taken from different cell types or different tissue types of one given organism, or may be extracts of different parts of a given plant. Those ligand-macromolecule interactions which appear in a plurality of different samples are those which have a higher likelihood of factually occurring.

To the extent the macromolecules in their entirety define a proteome and the ligands are naturally occurring molecules binding to the macromolecules in said proteome, the method of the first aspect provides for obtaining a protein-metabolite interactome (PMI).

Determining the PMI of a given biological system provides a number of advantages over existing approaches for lead identification and drug development.

First, knowing the PMI defines both the druggable proteins of that biological system as well as the chemical space of ligands binding to the druggable proteins. This helps in selecting both better targets for drug development as well as providing lead compounds for drug development.

In a preferred embodiment, comparing the PMIs of different tissues such as diseased versus healthy tissue is performed. This allows to identify interactions which occur only in diseased cells. These provide direct access to drug development specifically addressing druggable targets in diseased cells. An exemplary disease is cancer.

In another preferred embodiment, PMI of chloroplasts are analyzed and compared to other PMIs. Chloroplast-specific PMIs allow to develop plant-specific herbicides.

The term "protein-metabolite interactome" designates the entirety of interactions occurring between proteins and small molecules naturally occurring in a biological system. This is an art-established term. The term "metabolite" is a generic term designating small molecules occurring in biological systems and made by the action of enzymes in said systems. Small molecules include, but are not confined to amino acids, peptides, nucleosides, nucleotides, oligonucleotides, monosaccharides, disaccharides, oligosaccharides, fatty acids, monoacylglycerols, diacylglycerols, triacylglycerols, phospholipids and intermediates of the metabolism such as C6 and C3 molecules occurring in glycolysis or gluconeogenesis, tricarbocylic acids, pyruvate, lactate; and furthermore coenzymes, co-factors and prosthetic groups.

In a further preferred embodiment (i) said method of step (a) separates complexes and unbound ligands according to size and/or charge and preferably is size filtration, size exclusion chromatography (SEC), electrophoresis, centrifugation, thermophoresis and/or field flow fractionation (FFF); and/or (ii) said chemical analysis method is mass spectrometry (MS), nuclear magnetic resonance (NMR), sequencing and/or detection by antibodies.

As noted above, the method to be used in step (a) of the method of the first aspect may provide for a separation of analytes according to size. Separation may be such that small molecules pass faster than larger molecules. In the alternative, large molecules may pass faster than small molecules. Size filtration provides for retaining analytes to an increasing extent the larger they are. Size exclusion chromatography on the other hand provides for a higher degree of retention of analytes when they are smaller. Preferred devices and matrices for performing size filtration and size exclusion are well-known in the art. Exemplary or preferred materials and devices are mentioned in the examples enclosed herewith.

The term "size", in one embodiment, is the molecular mass. In other embodiments, "size" is an apparent size, apparent size being the parameter according to which separation in a given analytical method occurs. Apparent size may be the hydrodynamic volume. Apparent size and molecular mass will correlate, correlation preferably being governed by a monotonous function. Apparent size and molecular mass may coincide. Preferably, size is molecular mass.

In electrophoresis, smaller molecules migrate faster. Having said that, it has to be noted that in addition the charge status of the given analyte governs the electrophoretic mobility of a given molecule.

Centrifugation provides for more rapid sedimentation of larger analytes.

In thermophoresis, molecules are separated according to the Soret coefficient which is a function of size, hydration shell and charge; see, e.g. Duhr S, Braun D. Why molecules move along a temperature gradient. Proc Natl Acad Sci USA. 2006 Dec. 26; 103(52):19678-82. Epub 2006 Dec. 12. PubMed PMID: 17164337; PubMed Central PMCID: PMC1750914.

Field flow fractionation (FFF) is a separation method where a field is applied to a fluid suspension or solution. The suspension or solution is pumped through a channel. Perpendicular to the direction of flow through that channel, said field is applied. The term "field" in that context is rather broad and may be an electric field, a magnetic field, a centrifugal field, a thermal gradient or flow through a semi-permeable membrane. Accordingly, also the molecular properties governing separation in FFF may vary. Generally, there will be a function of size/hydrodynamic volume and/or charge.

Particularly preferred in accordance with the present invention are size filtration and size exclusion chromatography.

In a further preferred embodiment, said ligand is a non-covalent ligand.

In a particularly preferred embodiment, and to the extent said ligand is a non-covalent ligand, said releasing in step (b) is effected by denaturation of said complexes.

Once step (a) of the method of the first aspect has been completed, unbound ligands are removed from the mixture. Ligands are still present, however, only to the extent they are bound to macromolecules. In order to eventually determine said ligands, it is necessary to release them from the complexes. A preferred means is denaturation. Denaturation interferes with the 3-dimensional structure of the macromolecules, including their capability to bind a given ligand.

In a particularly preferred embodiment, said denaturation is effected by (ba) heating, preferably to 100° C.; (bb) adding denaturing chemicals such as chaotropic compounds including urea and guanidinium hydrochloride and detergents including SDS; (bc) adding organic solvents interfering with the ligand-macromolecule interaction such as acetone and acetonitrile; and/or cleaving said macromolecules enzymatically and/or chemically. Enzymatic cleavage can be done; e.g., with trypsin.

These means and methods of denaturation are art-established. Generally speaking, any art-established method for denaturing a macromolecule or a complex comprising a macromolecule is applicable, as long as it does not interfere with the integrity of the ligand.

In a further preferred embodiment, said method further comprises one, more or all of the following further steps: (aa) prior to step (a), breaking up cells comprising said macromolecules and optionally said ligands, followed by removal of insoluble material; (ab) after step (a) and prior to step (b), washing; (ca) after step (b) and prior to step (c), removing macromolecules, extracting ligands and/or performing liquid chromatography (LC) or gas chromatography (GC) of the ligands, or, if applicable, of the extracted ligands, wherein preferably said LC or GC, to the extent it is performed, is effected in an online LC/MS device, an online LC/NMR device, and online GC/MS device or an online GC/NMR device; (da) after step (b) and prior to step (d), to the extent step (d) is performed, extracting macromolecules and optionally performing LC of the extracted macromolecules, wherein preferably LC is effected in an online LC/MS device or online LC/NMR device.

Step (aa) provides for a step preceding step (a) which uses cells as starting material. These cells may be isolated cells or cells comprised in the tissue or biological sample. Upon breaking up said cells, insoluble material may be removed, for example by centrifugation. Further purification steps are less preferred and generally dispensable. Accordingly, step (aa), while providing for removal of insoluble material, preferably excludes any further processing, especially a purification step, prior to feeding the cell extract into step (a) of the method of the first aspect. Said cell extract is a preferred sample in accordance with step (a).

Washing in accordance with step (ab) is preferred because it provides for removal of any unbound material. Unbound materials are large analytes in case of size exclusion and small analytes in case of size filtration.

Step (b) of the method of the first aspect provides for releasing bound ligands from macromolecules. Prior to subjecting the released ligands to analysis in step (c) it is preferable to remove macromolecules in a step (ca). This can be done, for example by centrifugation. In particular, if denaturation has been used for the purpose of releasing ligands, denatured macromolecules are easily removed by means of centrifugation.

Extracting ligands can be done as described in Giavalisco, et al. (*Plant J.* 68, 364-76 (2011)). Generally speaking, mixtures of water with polar solvents can be used for extracting. A particularly preferred solvent mixture for extraction is the ternary mixture of methyl tertiary butyl ether (MTBE), methanol and water. This is particularly useful for extracting semi-polar ligands. This is also useful for simultaneous precipitation of macromolecules which are subsequently pelleted.

Extracting macromolecules, especially proteins can be done in parallel to ligand extraction using the MTBE method (see above) or using other extraction methods like aceton, methanol/chloroform, or proteins can be directly solubilized in a urea/thiourea mixture or detergents prior to chemical analysis.

In relation to the first aspect, the present invention also provides a method of determining ligands of proteins, said method comprising or consisting of (a) subjecting complexes formed by said proteins and said ligands to size filtration or size exclusion chromatography; (b) denaturing, for one, more or all fractions obtained in step (a), said complexes; (c) subjecting the released ligands obtained in step (b) to mass spectrometry (MS), thereby determining said ligands of said macromolecules; (d) subjecting the released macromolecules obtained in step (b) to MS, thereby determining said macromolecules; and (e) comparing elution profiles of ligands with elution profiles macromolecules, thereby determining which ligand binds which macromolecule.

In a second aspect, the present invention provides a method of identifying, out of a plurality of test compounds, (a) ligand(s) of one or a plurality of macromolecules, said method comprising or consisting of: (a) bringing said macromolecule(s) into contact with said plurality of test compounds; (b) subjecting the mixture obtained in step (a) to a method which separates complexes, if any, formed between said macromolecule(s) and (a) ligand(s) from unbound test compounds; (c) dissociating complexes, thereby releasing bound ligands, if any, from macromolecules; and (d) subjecting the released ligand(s) obtained in step (c), if any, to a chemical analysis method, thereby identifying a ligand(s) of said macromolecule(s).

Definitions and explanations as given in relation to the method of the first aspect and preferred embodiments thereof apply mutatis mutandis to the second aspect of the present invention.

Complexes and ligands in accordance with the second aspect are non-covalent complexes and non-covalent ligands, respectively.

The method of the second aspect is a screening method. Deviant from the prior art methods which typically require that in each assay only a single test compound is assayed for its potential capability of binding to a macromolecule, the present invention provides for the concomitant assaying of a plurality of ligands. The number of ligands is not particularly limited in that respect and may be up to 1000, up to 10000, up to 100000, up to 1000000 or more. Furthermore, also several macromolecules may be assayed concomitantly in the same mixture. Accordingly, multiplexing with regard to ligands is conveniently affordable. Moreover, even two-dimensional multiplexing, namely with regard to both ligands and macromolecules is achievable.

Especially to the extent one macromolecule is used in the method of the second aspect, in particular a known macromolecule, determining said macromolecule is obviously dispensable.

On the other hand, to the extent a plurality of macromolecules is used in the method of the second aspect, it is preferred that one or more macromolecules are determined by a chemical analysis method.

It is particularly preferred that after steps (d) and (e), (f) it is determined which ligand binds which macromolecule, preferably by comparing elution profiles of ligands to elution profiles of macromolecules.

In a preferred embodiment of the second aspect, (i) said macromolecule(s) is/are (a) protein(s) or (a) nucleic acid(s), preferably RNAs; (ii) said ligand(s) is/are as defined in relation to the first aspect and preferred embodiments thereof; and/or (iii) said plurality of macromolecules are 2, 3, 4, 5, 6, 7, 8, 9 or 10 macromolecules.

In a further preferred embodiment of the second aspect, (i) said method of step (b) is size filtration chromatography, size exclusion chromatography, electrophoresis, centrifugation, thermophoresis and/or FFF; and/or (ii) said chemical analysis method of step (d) is mass spectrometry (MS) or nuclear magnetic resonance (NMR).

In a further preferred embodiment, said dissociating in step (c) is effected by denaturation of said complexes, said denaturation preferably being effected by (ca) heating, preferably to 100° C.; (cb) adding denaturing chemicals such as chaotropic compounds including urea and guanidinium hydrochloride and detergents including SDS; and/or (cc) adding organic solvents interfering with the ligand-macromolecule interaction such as acetone and acetonitrile; and/or (cd) cleaving said macromolecules enzymatically and/or chemically.

In a further preferred embodiment, said method further comprises one, more or all of the following further steps: (ba) after step (b) and prior to step (c), washing; (da) after step (c) and prior to step (d), removing said macromolecule(s), and extracting ligand(s), if any.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: Experimental work flow. Cells were extracted using native TMN buffer (Steps 1-2). Native soluble fraction was obtained by ultracentrifugation step (Step 3). Size filtration was performed using 10 kDa spin columns. Heat denaturation was applied to release complex bound small molecules (Step 4a). Alternatively, protein-metabolite complexes were separated from free metabolites using SEC (Step 4b). Collected samples were subjected to all-in-one MTBE-methanol-water metabolite and protein extraction (Step 5). Semi-polar metabolites were quantified by LC/MS (Step 5).

Figure 2:
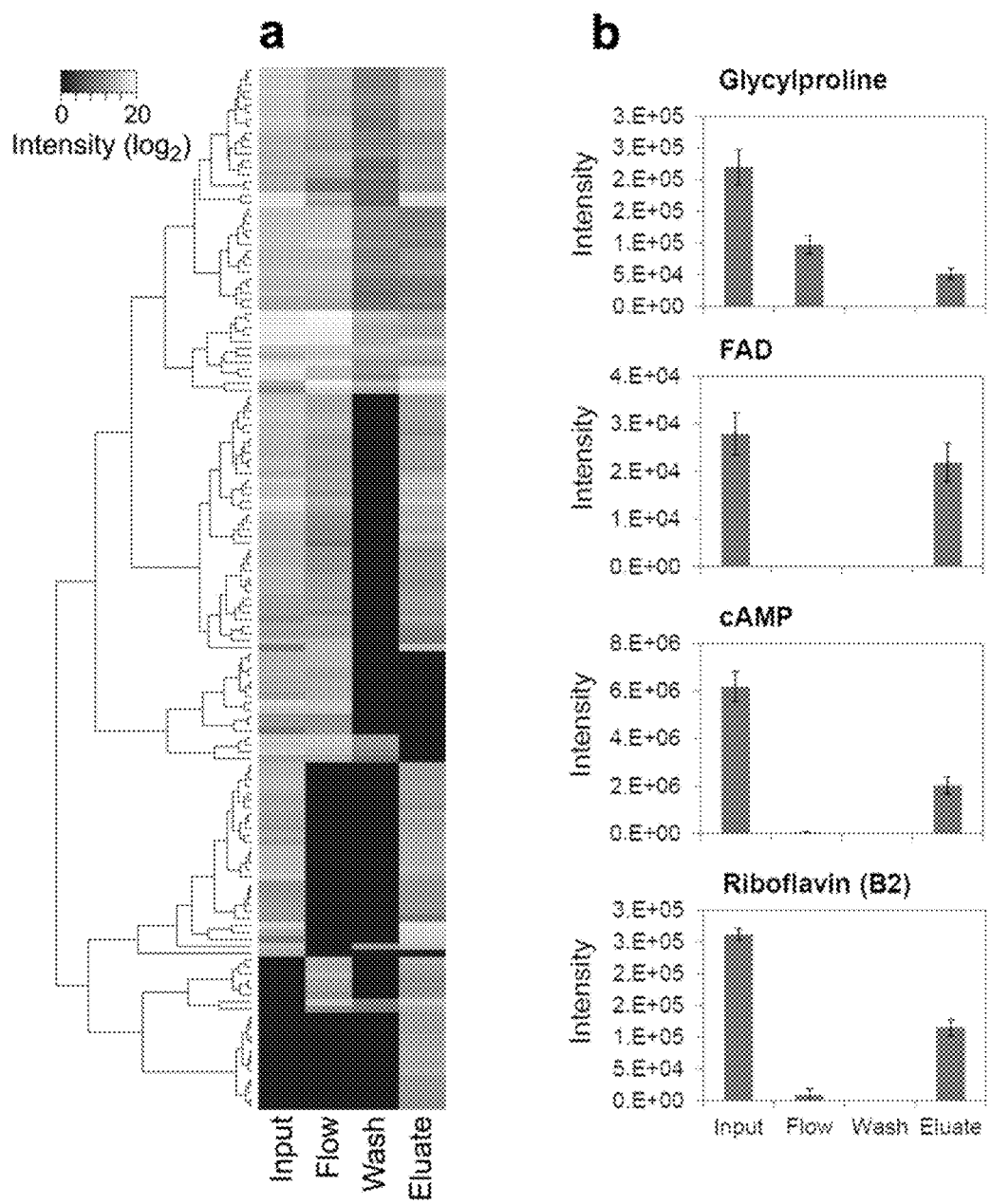

FIG. 2: Size filtration separates protein bound from free small molecules. Presented here is the subset of those that could be putatively annotated to a sum formula using $^{15}$N and $^{13}$C labeling information (Giavalisco (2011), loc. cit.) and/or to a metabolite using reference compounds. Note that annotation was focused on mass features present in the eluate and therefore classified as complex bound.

Figure 3:
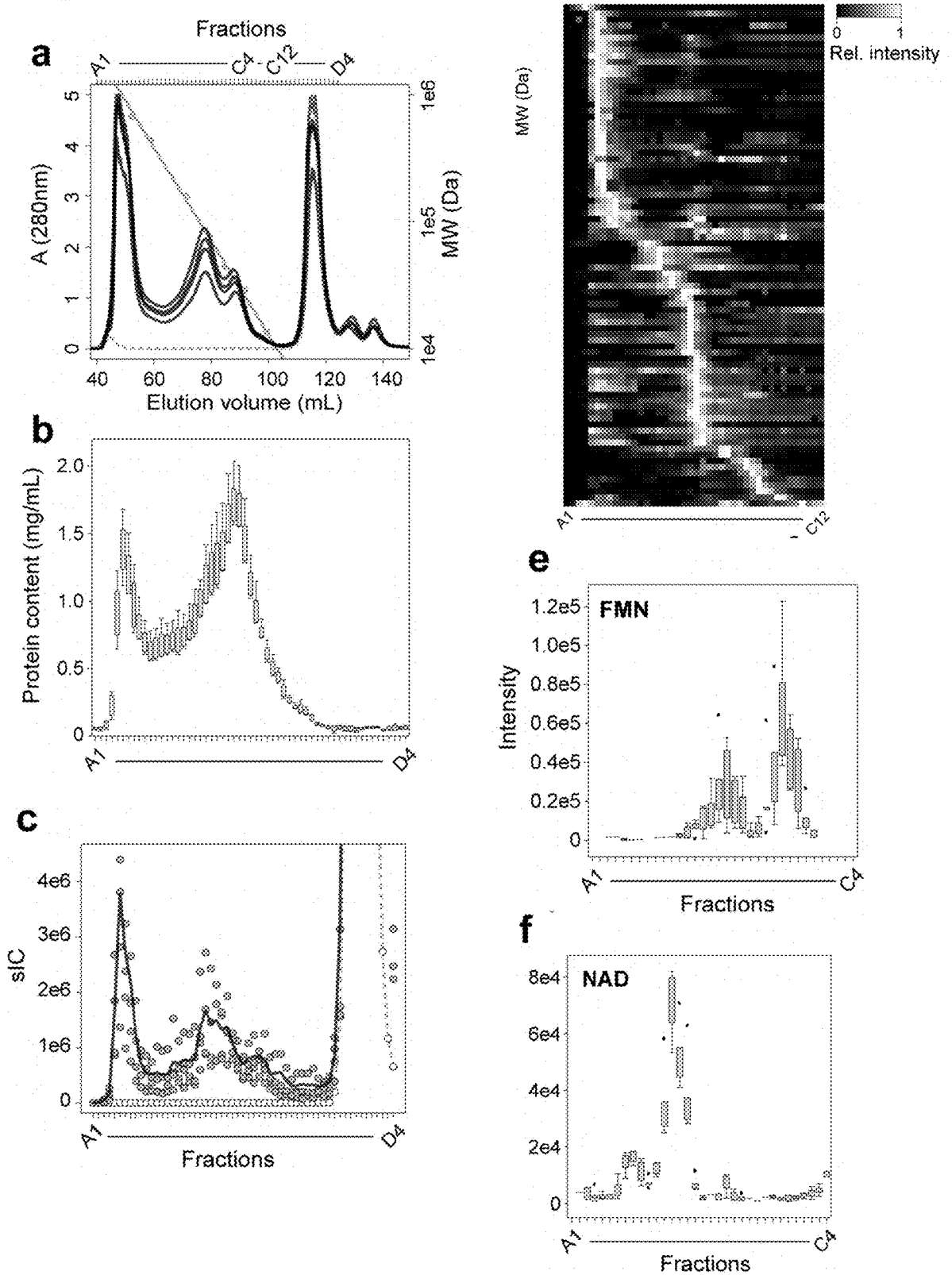

FIG. 3: SEC separates protein bound from free small molecules. (a) Chromatograms of the absorption at 280 nm of four SEC replicates (black) and the non-protein control (dotted line). The approximate molecular mass distribution as determined from a standard curve is plotted in grey. (B) Protein content of the 57 analyzed fractions from SEC analysis. (C) Summed ion count across SEC fractions of 83 selected small molecules plotted in (D) of independent experiments (circles) and their mean (lines). (D) Heat map of SEC profiles of 83 selected small molecules from the size filtration experiment in 42 fractions greater 10 kDa (z-score of the mean of n=4 experiments). Exemplary SEC profiles of the co-factors FMN (E) and NAD (F).

Figure 4:
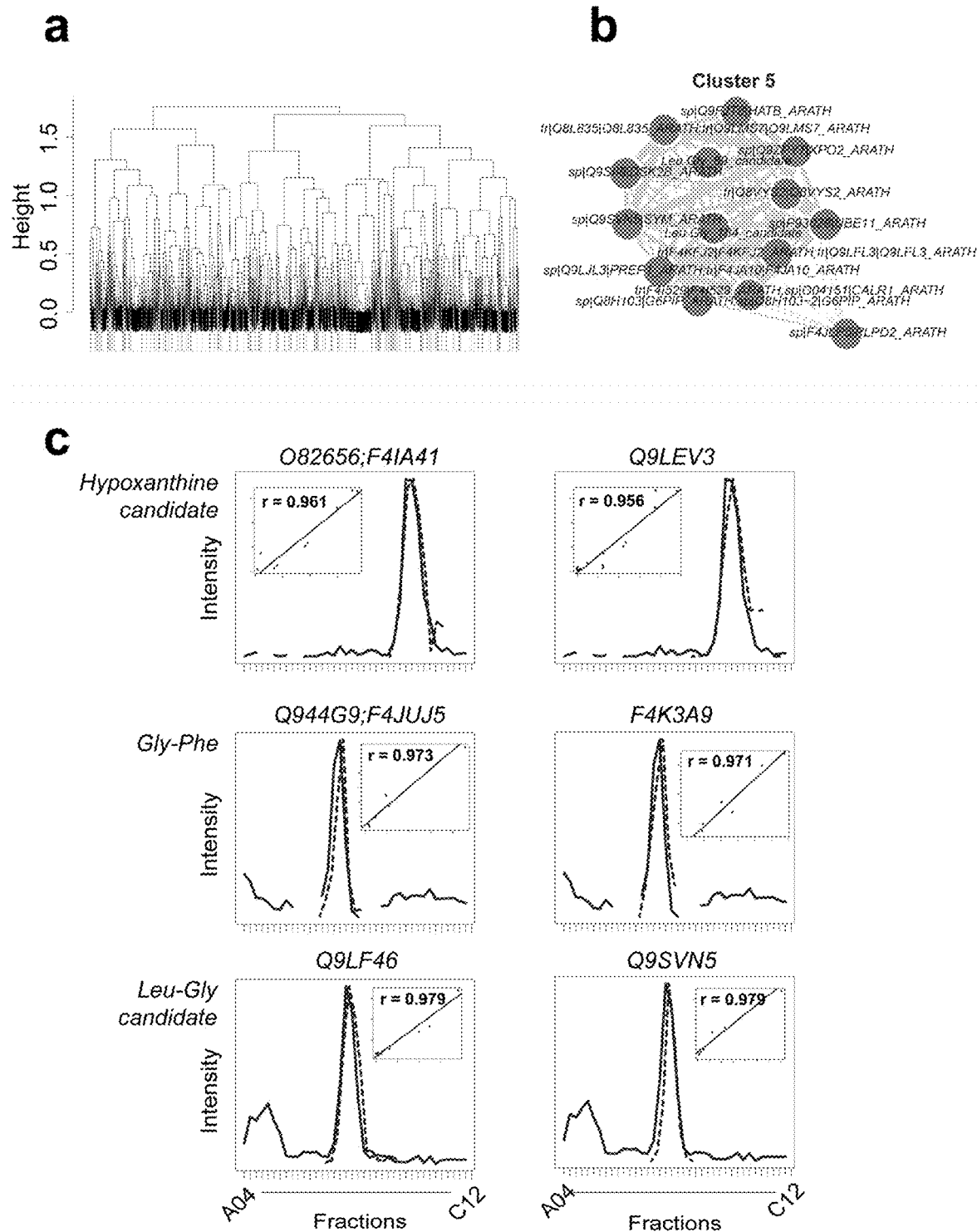

FIG. 4: Results of co-fractionating analysis. See also Example 5.

Figure 5:
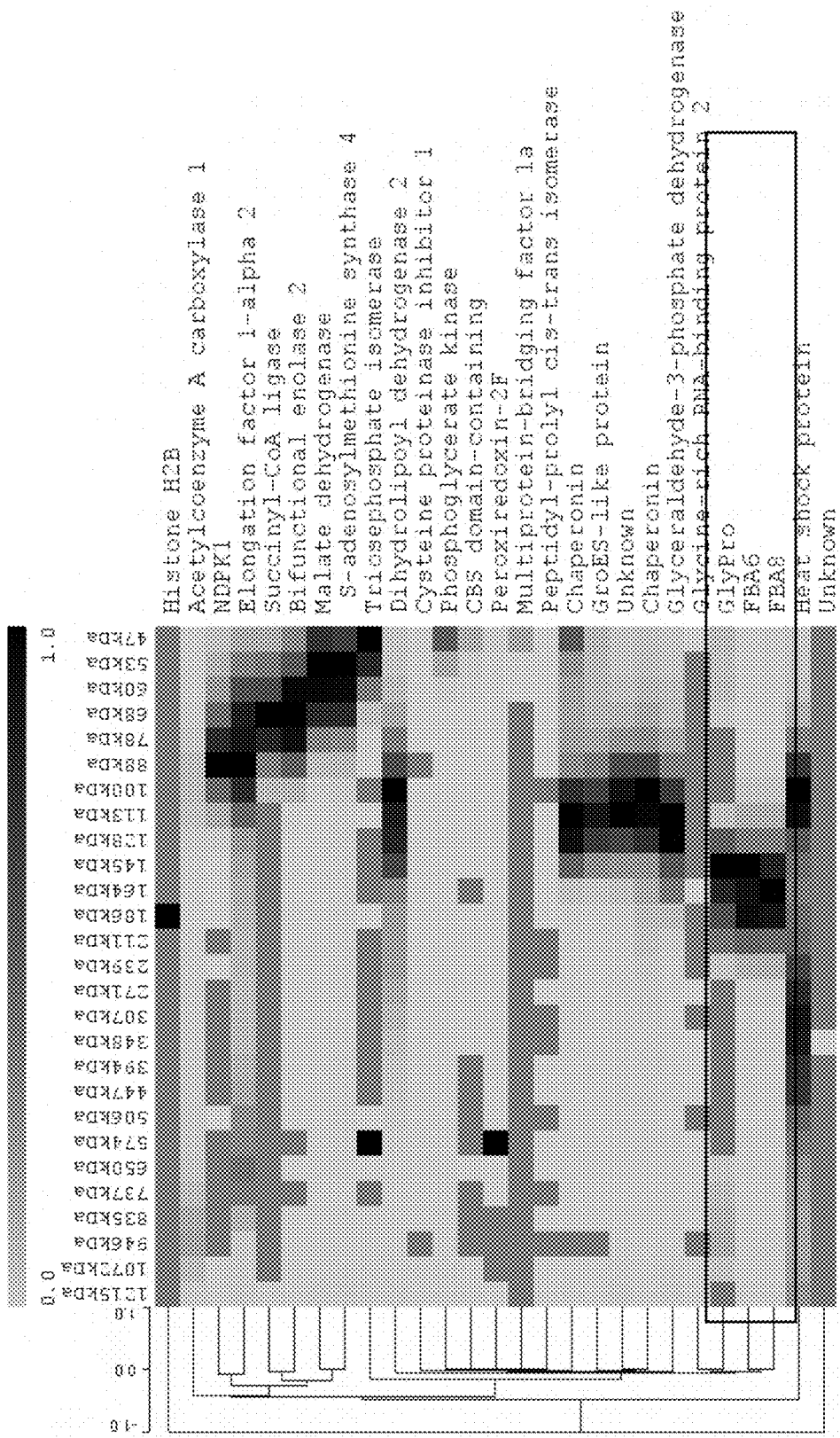

FIG. 5: Combined figure presenting elution profile of proteins captured with the Gly-Pro affinity beads across protein containing fractions in the SEC experiment. Also given is Gly-Pro elution pattern measured in the SEC experiment. Data are normalized to the maximal intensity measured in the SEC separation. Indicated with frame Gly-Pro co-elution with FBA6 and FBA8.

Figure 6:
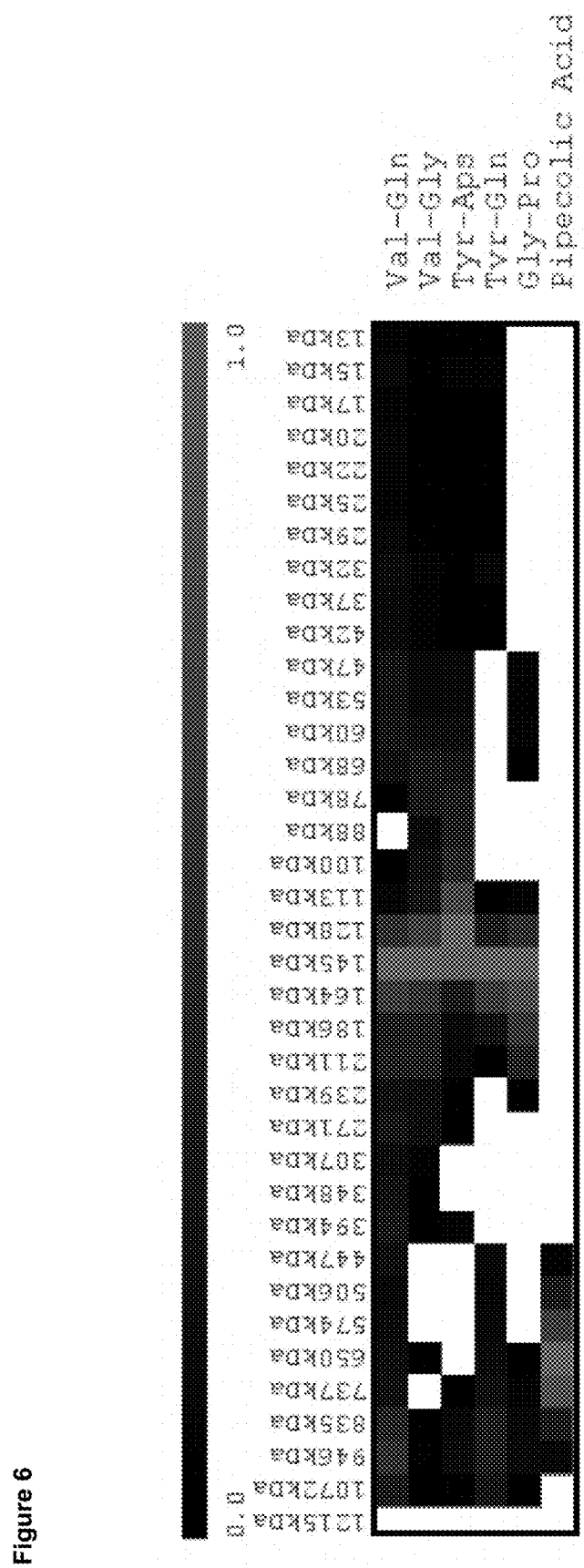

FIG. 6: Combined figure presenting elution profile of metabolites captured with the affinity tagged FBA6 across protein containing fractions in the SEC experiment. Data are normalized to the maximal intensity measured in the SEC separation. Note that in addition to Gly-Pro, and with the exception of pipecolic acid, all the other small molecules pulled with FBA6 co-elute with FBA6 in the SEC experiment. It is therefore likely, that not one but number of different dipeptides can interact with FBA6.

Figure 7:
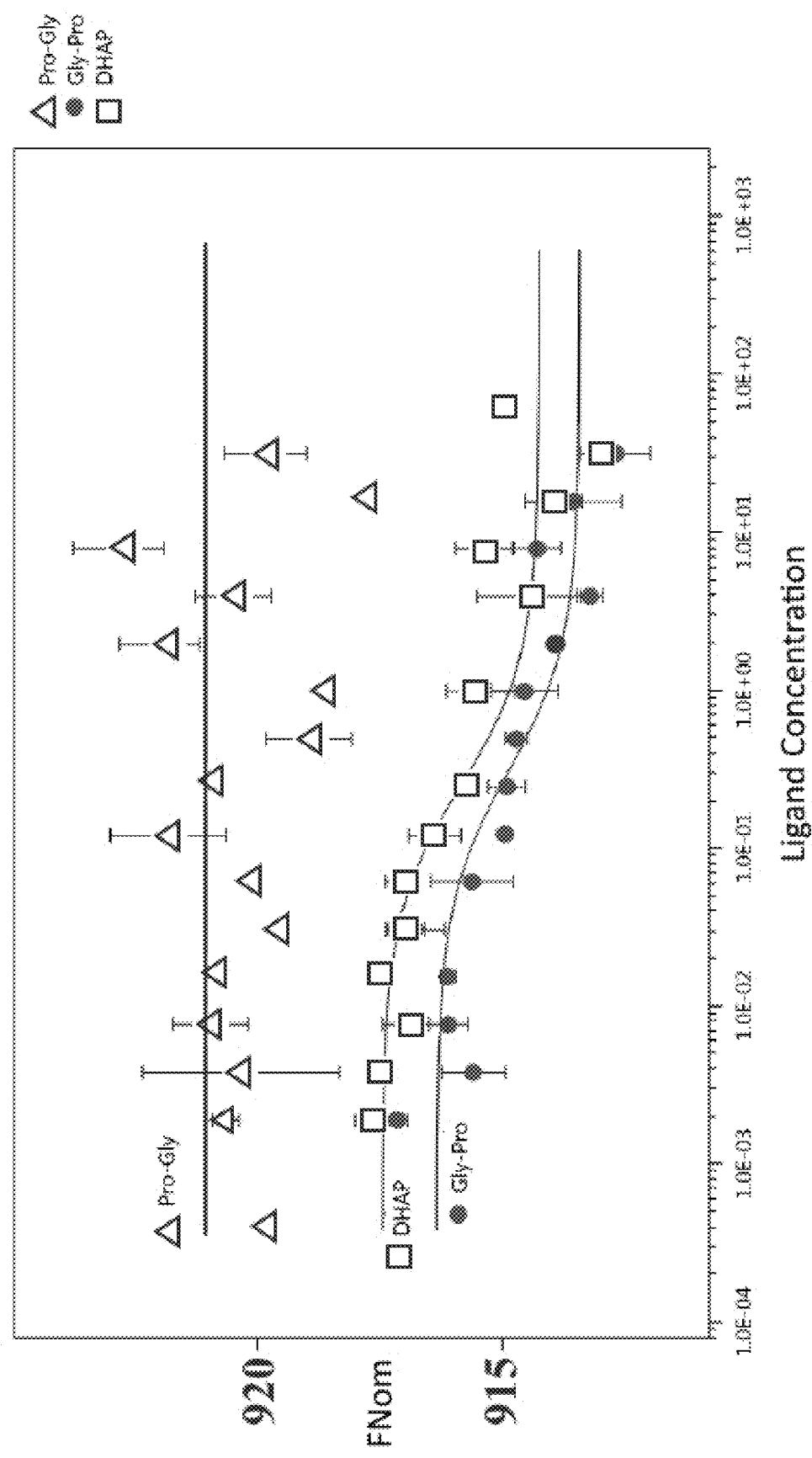

FIG. 7: DHAP (substrate) and Gly-Pro, but not Pro-Gly, bind FBA6 with Kd of approximately 200 nM.

Figure 8:
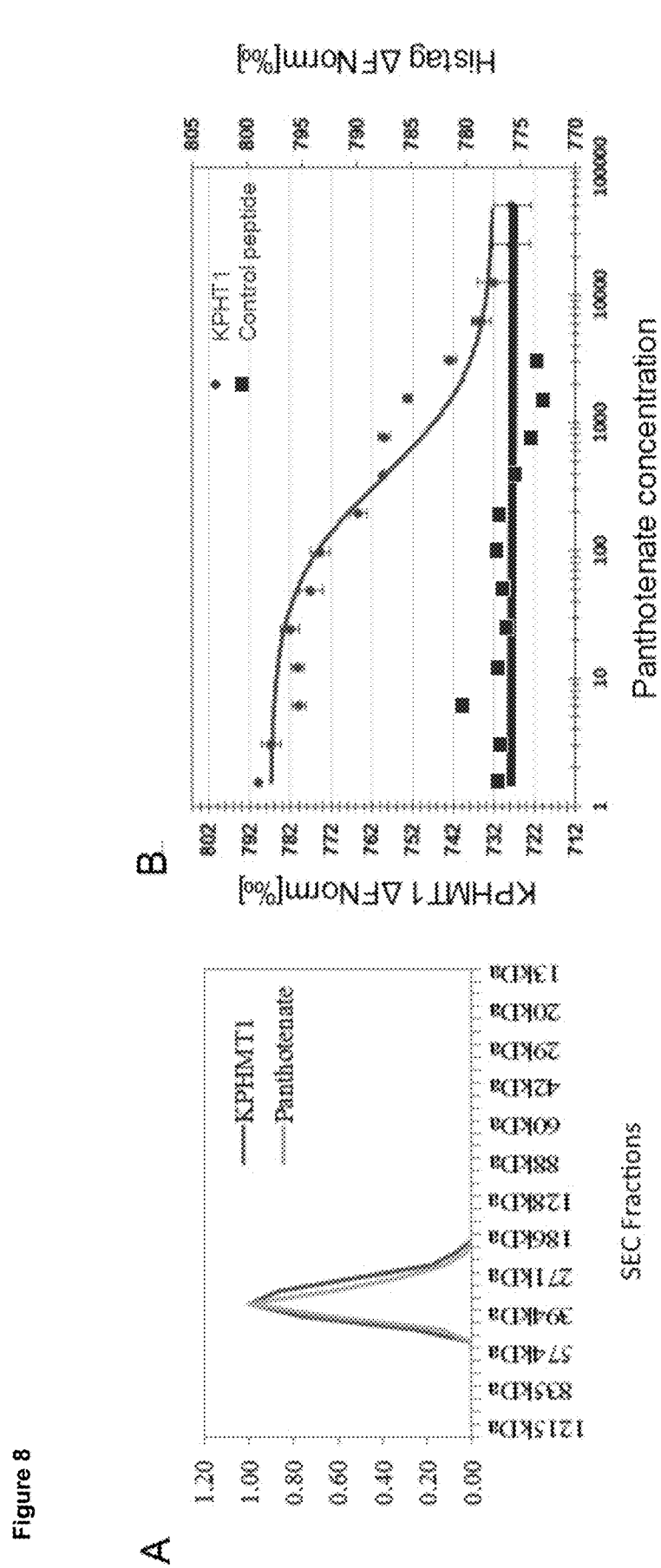

FIG. 8: Panthotenate interact with 3-methyl-2 oxobutanoate hydroxymethyl-transferase 1 (KPHMT1).
A) Panthotenate co-elutes with KPHMT1 across protein-containing fractions in the SEC experiment, person correlation r=0.93.
B) Panthotenate-KPHMT1 interaction was tested by Microscale thermophoresis (MST) assay. Data are presented as difference in normalized fluorescence (ΔFNorm) calculated between bound and nonbound KPHMT1 with a Kd of 367.4 µM. As control peptide a 6×Histag peptide was assayed in a presence of MTA, no binding was observed. Data are mean±SD, n=3.

Figure 9:
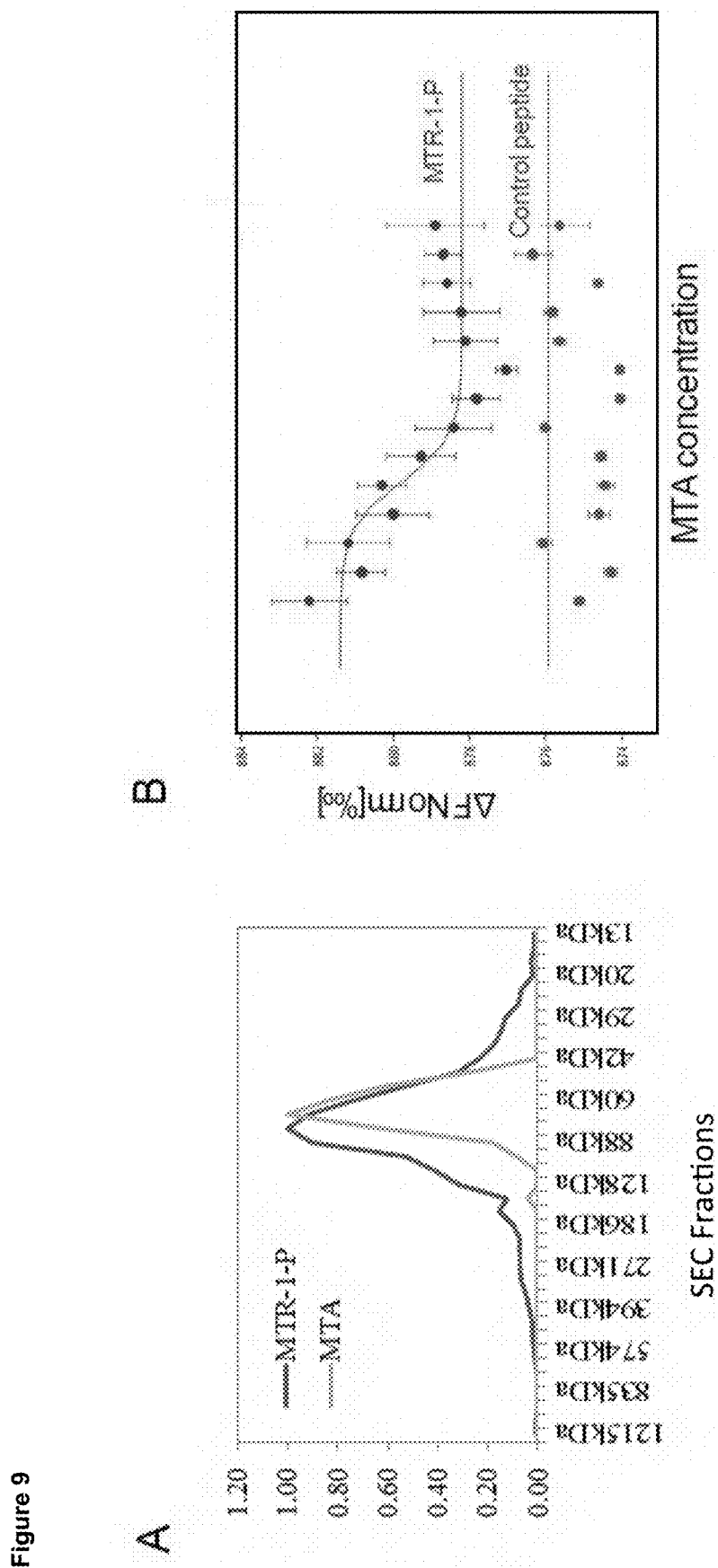

FIG. 9: Methylthioadenosine (MTA) interact with Methylthioribose-1-phosphate isomerase (MTR-1-P).
A) Co-elution of MTA and MTR-1-P across protein-containing fractions in the SEC experiment with a person correlation r=0.75.
B) MTA-MTR-1-P interaction was tested by Microscale thermophoresis (MST) assay, Data are presented as difference in normalized fluorescence (ΔFNorm) calculated between bound and nonbound MTR-1-P with a Kd of 2.7 µM. As control peptide a 6× Histag peptide was assayed in a presence of MTA, no binding was observed. Data are mean±SD, n=3.

Figure 10:
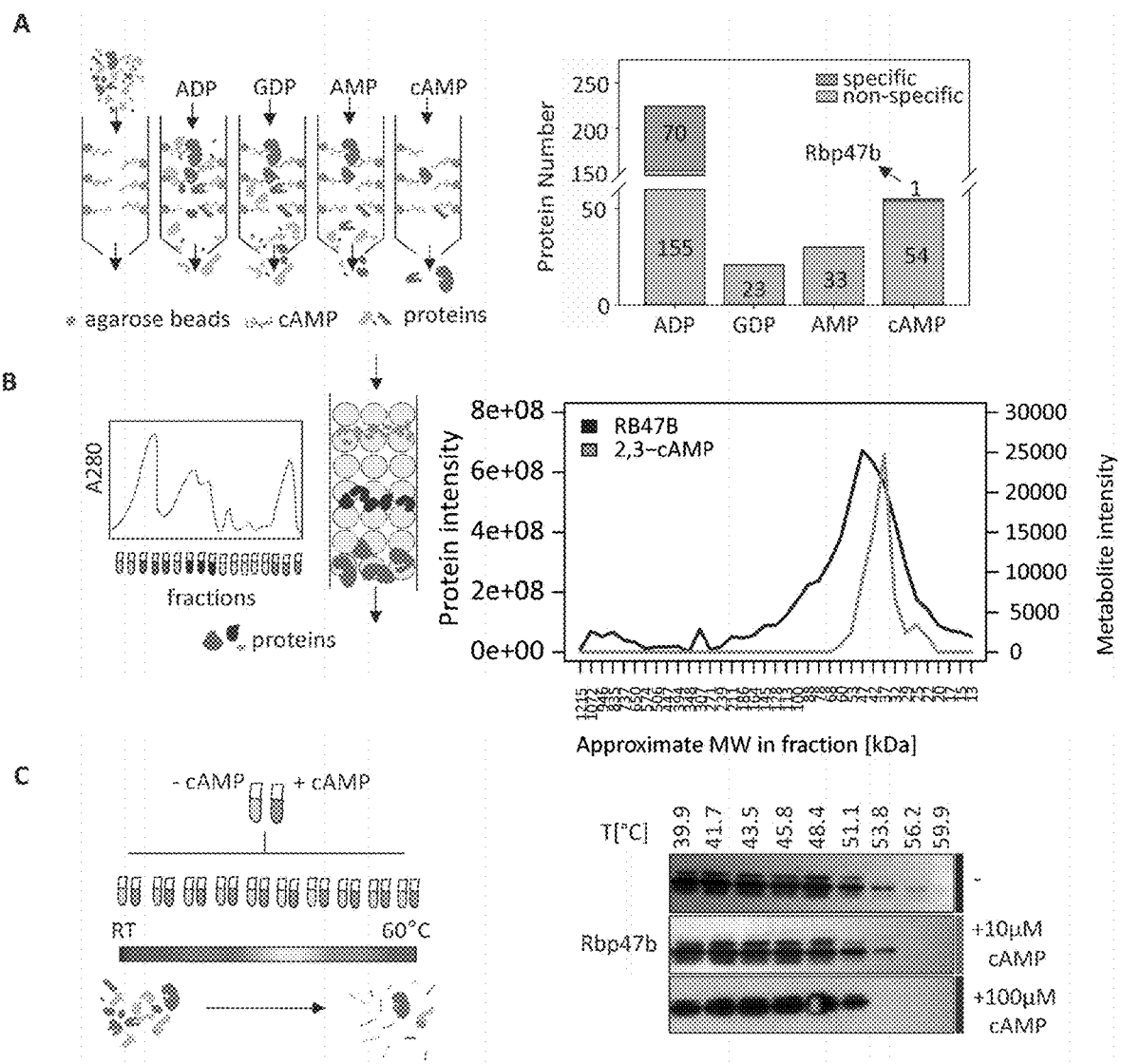

FIG. 10: 2',3'-cAMP binds to the Rbp47b protein in native cellular extract.
(A) Schematic representation of the affinity-purification experiment with the four sequential elution steps (left panel). The experiment was done in triplicate. Specific proteins are defined as present in only one elution, in all three independent samples. Non-specific proteins are defined as present in more than one elution (right panel). (B) Schematic representation of the SEC experiment (left panel); co-elution of 2',3'-cAMP and Rbp47b across protein-containing fractions in the SEC experiment (right panel). Data are normalized to the maximal intensity and are given as means of 3 (protein) or 4 (metabolite) independent experiments. (C) Schematic representation of the thermal stability assay (left panel); western blot analysis of Rbp47b-TAP protein abundance (right panel). Presented experiment was repeated three times.

Figure 11:
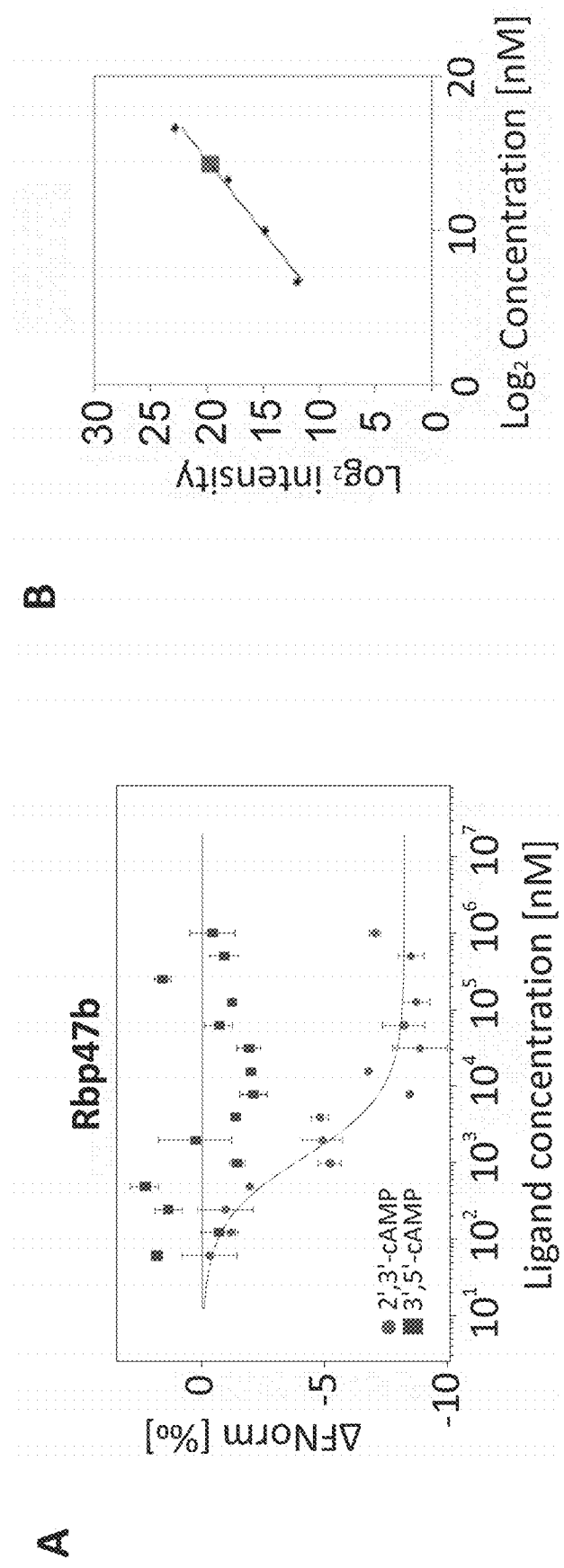

FIG. 11: 2',3'-cAMP binds to Rbp47b protein in vitro. (A) MST measurements testing the interaction between Rbp47b and 2',3'-cAMP/3',5'-cAMP. Data are presented as difference in normalized fluorescence (ΔFNorm) calculated between bound and non-bound Rbp47b. Data are mean±SD, n=3 (technical replication). Kd of the Rbp47b-2',3'-cAMP interaction was calculated at 1.02 µM. (B) Log 2 of 2',3'-cAMP intensity measured in Arabidopsis native lysate (square) was plotted against the calibration curve (points) used to calculate absolute 2',3'-cAMP concentration from the LC-MS metabolite measurements (mean±SD, n=3). Samples were from one experiment.

Figure 12:
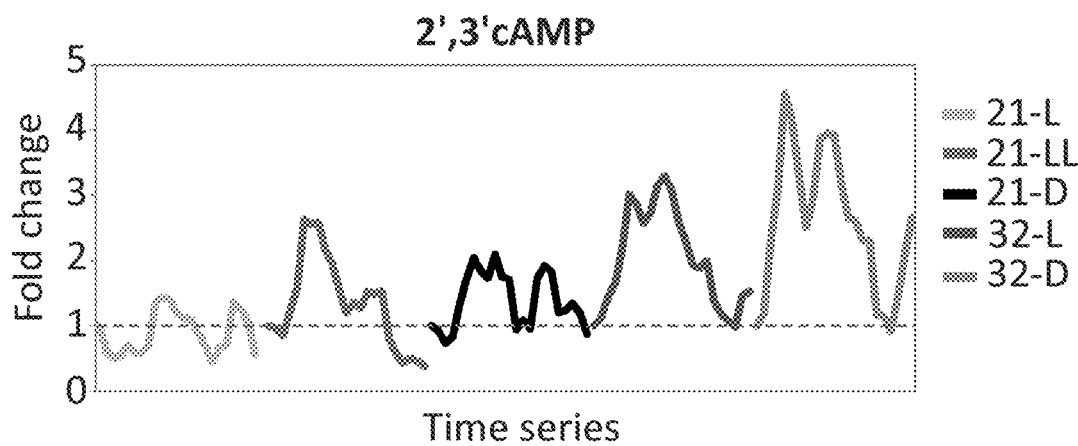
Figure 12:
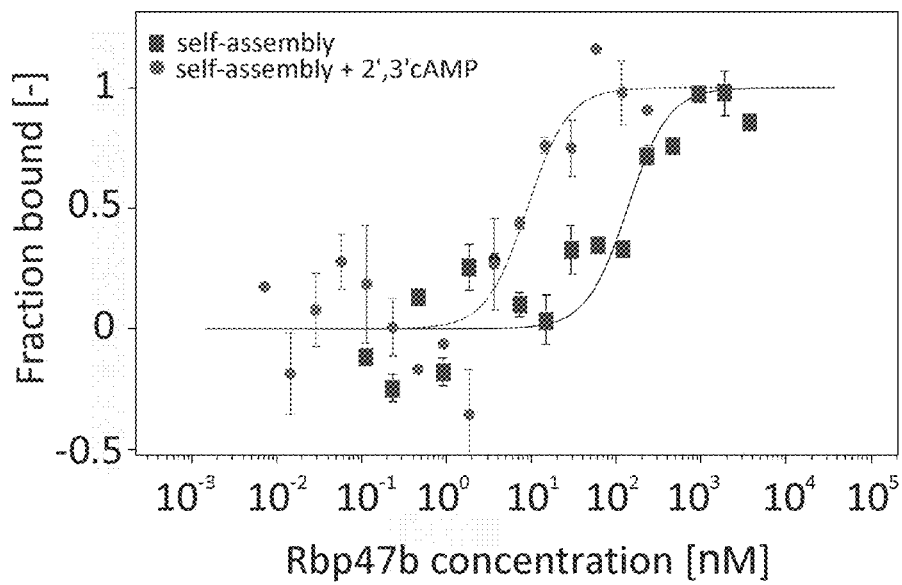

FIG. 12: 2',3'-cAMP accumulates in response to stress conditions and promotes Rbp47b self-assembly.
(A) 2',3'-cAMP accumulation in mature Arabidopsis rosettes under different stress conditions 31. Data are presented as moving average of 2',3'-cAMP intensity normalized to time point 0. The first samples were taken at 5, 10, and 20 min following stress onset and afterwards every 20 min until 6 h. The last two samples were taken after 10 and 20 h after stress onset. 21: 21° C. (control condition), 32: 32° C. (heat stress), L: control light condition (150 µE m−2 sec−1), LL: low light (70 µE m−2 sec−1), D: darkness. Data are means of three independent measurements. (B) MST measurement of the Rbp47b self-assembly in the presence (Kd=8.9 nM) or absence (Kd=127.87 nM) of 50 µM 2',3'-cAMP. Data are presented as bound and non-bound protein. Data are mean±SD, n=2 (technical replication).

Figure 13:
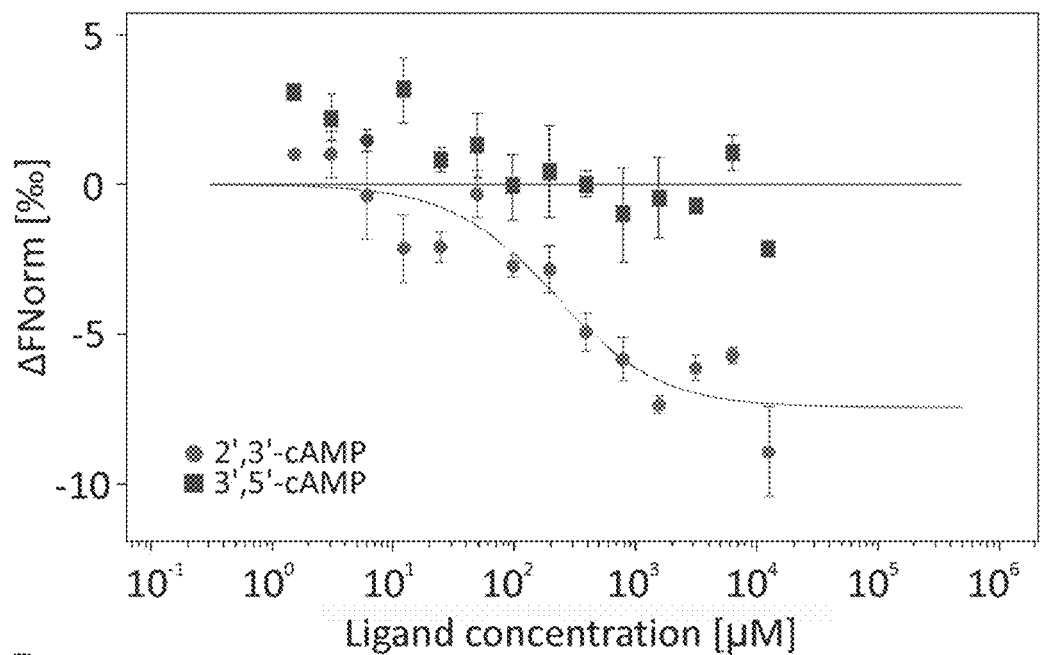
Figure 13:
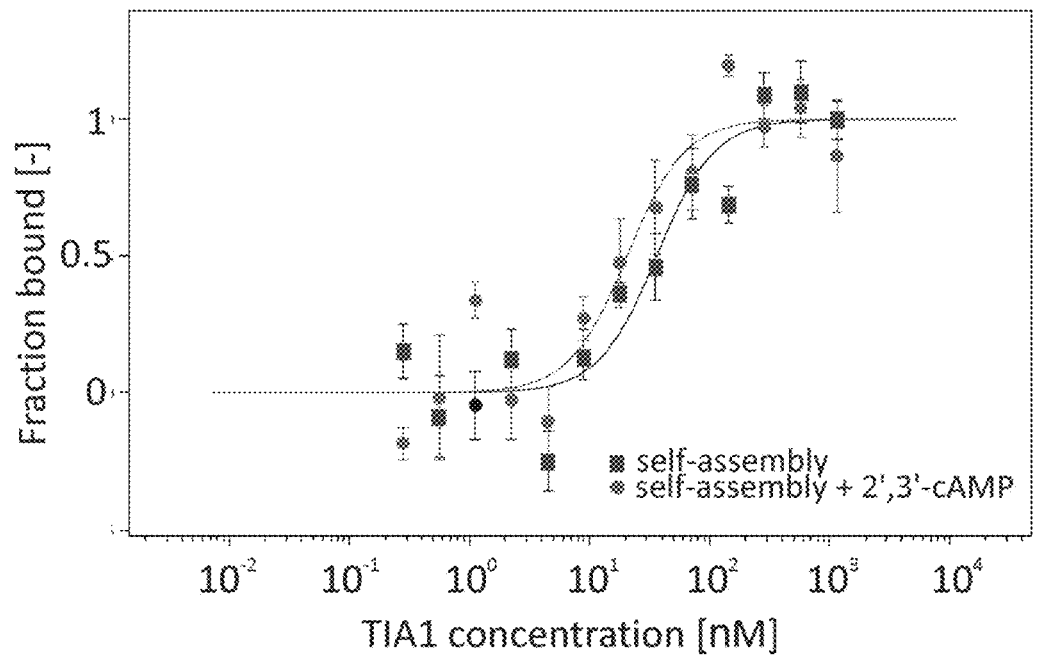

FIG. 13: 2',3'-cAMP binds to human homolog of Rbp47b-TIA1 and promotes its oligomerization.
(A) MST measurement of interaction between TIA1 and 2',3'-cAMP/3',5'-cAMP. Data represent difference in normalized fluorescence (ΔFNorm) calculated between bound and non-bound TIA1. Data are mean±SD, n=3 (technical replication). Kd of the TIA1-2',3'-cAMP interaction was calculated at 217 µM. (B) MST measurement of TIA1 self-assembly in the presence (Kd=20.55 nM) or absence (Kd=36.28 nM) of 500 µM 2',3'-cAMP. Data are presented as fraction bound, meaning bound and non-bound protein. Data are mean±SD, n=3 (technical replication).

Figure 14:
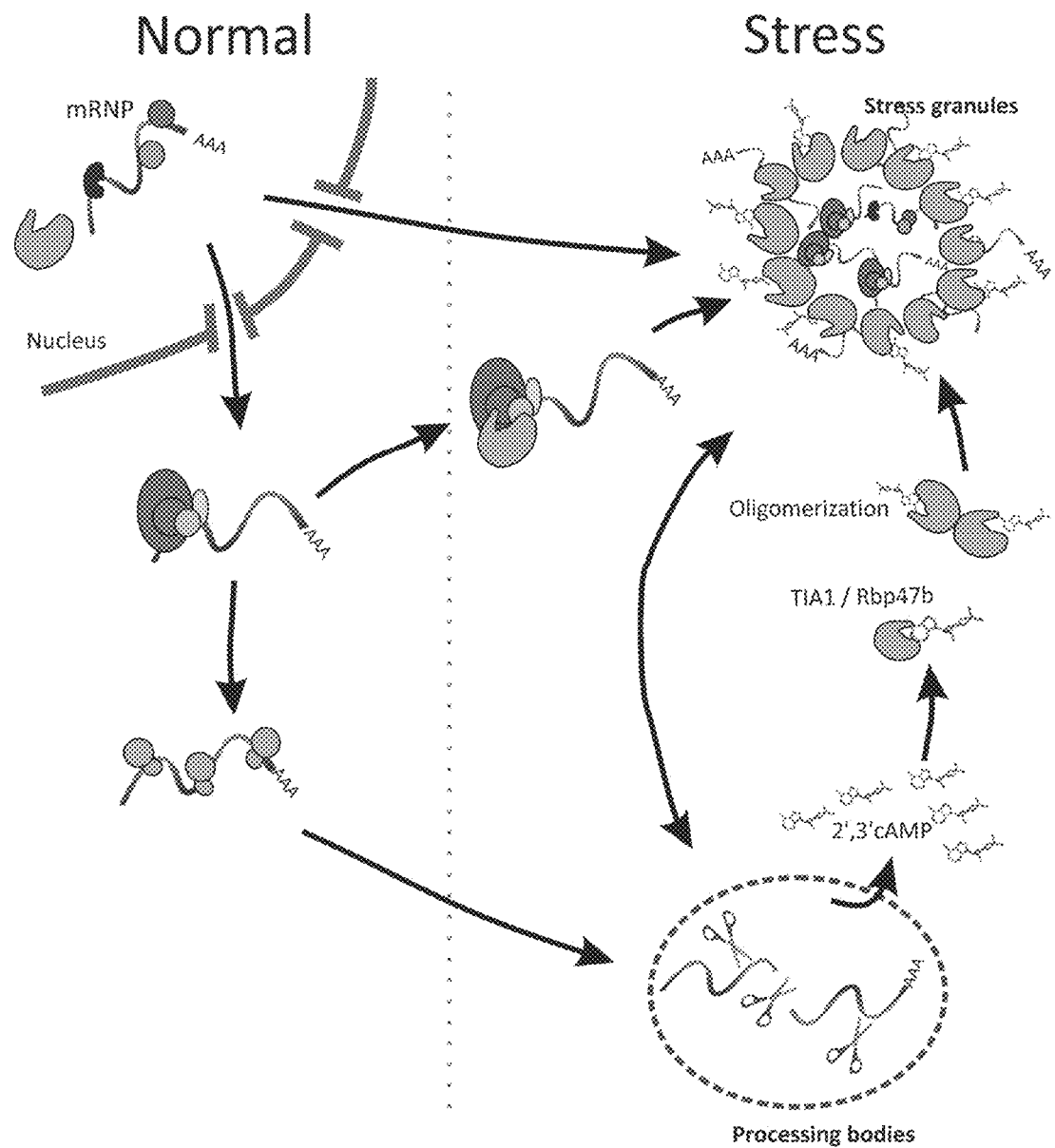

FIG. 14: Proposed role of 2',3'-cAMP in the regulation of the RNA fate. Under optimal conditions protein translation occurs and TIA1/Rbp47b is localized in the nucleus. Upon stress and as consequence of stalled translation mRNA degradation is triggered in processing bodies, leading to the accumulation of 2',3'-cAMP. Also under stress conditions TIA1/Rbp47b is exported to the cytosol, where it can form complexes with 2',3'-cAMP. The latter promotes TIA1/Rbp47b self-assembly and thus stress-granule formation, where RNA is stored and protected from degradation.

The examples illustrate the invention.

EXAMPLE 1

Materials and Methods
Growth of Arabidopsis Cell Cultures
MM2d Arabidopsis cells cultures (Menges & Murray, Plant J. 30, 203-12 (2002)) were grown in MSMO medium supplemented with 3% sucrose, 0.05 mg/L kinetin and 0.5 mg/L 1-Naphthaleneacetic acid on orbital shaker at 130 rpm in the light. Cells were passaged weekly to fresh medium and harvested during logarithmic growth using rapid filtration and liquid nitrogen snap freezing.
Cell Lysis and Preparation of Soluble Protein Fraction Frozen cells were grinded with mortar and pestle or a Retsch mill (Retsch GmbH, Haan, Germany) for 4 times 1 min at 30 rps. 1.5 mL (for size filtration) or 0.7 mL (for size exclusion chromatography) of lysis buffer (50 mM Tris-HCl pH 7.5, 500 mM NaCl, 1.5 mM $MgCl_2$, 5 mM DTT, 1 mM PMSF, 1×Protease Inhibitor Cocktail (Sigma-Aldrich), 0.1 mM $Na_3VO_4$ and 1 mM NaF) were added per 1 g of cells. In SEC experiments, 50 mM Ammonium bicarbonate-HCl pH 7.5 was used instead of Tris as buffering agent. After thawing on ice the extract was filtered through miracloth and subsequently centrifuged 10 min at 3452 g, 4° C. Ultracentrifugation 45 min at 35000 rpm (max 165052 g, avg 125812 g), 4° C. was used to prepare soluble fraction.
Size Filtration
2.5-3 ml of soluble fraction (see above) was filtered using Amicon 10 kDa Ultra centrifugal filter units (Millipore). At this stage 400 µL aliquots of input and flow-through were kept for metabolic analysis. Two washing steps, first using 5 mL and second 1.5 mL of wash buffer (50 mM TrisHCl pH 7.5, 500 mM NaCl, 1.5 mM $MgCl_2$, TNM) were applied to get rid of the remaining free metabolites. Approximately 1.5 mL of wash buffer was added to the column to cover the filter and 10 min, 100° C. treatment was used to denature proteins and so dissociate protein-metabolite complexes. 1 ml-1.2 mL aliquots from 2nd wash step and elute were kept for metabolic analysis. Centrifugation steps were performed at 3452 g for 15-30 minutes.
Size Exclusion Chromatography
2.5 mL of soluble fraction corresponding to 50 mg of protein for the separation. SEC was performed with a HiLoad 16/600 Superdex 200 prep grade column (GE Healthcare Life Science, Little Chalfont, UK) connected to an ÄKTA explorer 10 (GE Healthcare Life Science, Little Chalfont, UK) operating at 4° C. The flow rate was set to 0.8 mL/min. 57 fractions of 1.5 mL were collected from 40 to 125.5 mL elution volume of which 1 mL was dried in a speed-vac overnight and stored at −80° C. for metabolomic analysis. For the protein-free control experiment, 50 mg of protein of the soluble fraction was precipitated with 80% Acetone at −20° C. for 5 h. After pelleting denatured proteins by centrifugation at 3452 g for 20 min at 4° C., the supernatant was dried overnight in a speed-vac. All not precipitated small molecules were resuspended the next day in the original volume of lysis buffer and used for SEC.
Metabolite Extraction and LC/MS Metabolomics
Samples were extracted as defined in Giavalisco (2011), loc. cit. In essence, this method uses a methyl tert-butyl ether (MTBE)/methanol/water solvent system to separate proteins, lipids, and polar compounds into pellet, organic, and aqueous phases, respectively. After extraction, the aqueous phase was dried in speed-vac and stored at −80° C. until LC/MS analysis. Samples were measured using ultra-performance liquid chromatography coupled to an Exactive mass spectrometer (Thermo-Fisher; http://www.thermofisher.com) in positive and negative ionization mode as described in Giavalisco (2011), loc. cit. Processing of chromatograms, peak detection, and integration were performed using REFINER MS 7.5 (GeneData; http://www.genedata.com). Processing of mass spectrometry data included the removal of the isotopic peaks, as well as chemical noise. Obtained metabolic features (m/z at a given retention time) were queried against an in-house standard database and/or Metlin database (https://metlin.scripps.edu/index.php) (allowing 7 ppm error). Where available information on number of carbon and nitrogen atoms in a given feature was retrieved from metabolic profiles of cells labeled with $^{13}C$ or $^{15}N$ (analogous to Giavalisco (2011), loc. cit.).

EXAMPLE 2

Analysis of Ligands in Size Filtration

Native Arabidopsis MM2d cell culture lysate (later referred to as input) was loaded on size filtration spin columns with a 10 kDa cutoff to separate the protein fraction from the free metabolite fraction (flow through). Subsequently the protein fraction was washed thoroughly in order to remove any non-bound metabolites (wash). In a final step heat denaturation was applied to denature the proteins and release non-covalently bound metabolites from the proteins (elution). All samples were analyzed by applying our LC/MS metabolomics platform for semi-polar compounds (Giavalisco (2011), loc.cit.) (FIG. 1, step 5). Overall, LC/MS analysis of input, flow, wash and eluate samples resulted in approximately 8892 metabolic features (as defined by molecular mass (m/z) and retention time), of which approximately 150 could be putatively annotated to a metabolite. The flow through contained many metabolites and the metabolite content decreased in the washing. Strikingly, after heat treatment many metabolites (approximately 50% of all detected metabolic features), while being absent in wash samples, were again detectable in the eluate, thereby showing that this large fraction of metabolites is indeed forming stable complexes with proteins. Among these were well-known ligands such as cyclic nucleotides (cGMP, cAMP, cCMP), co-factors (FAD, NAD, FMN) and peptides (FIG. 2a-b). Proteins were digested on the cutoff filter and peptides were released for further analysis.

These results show that in the biological system analyzed there are numerous metabolites/small molecules forming a noncovalent but stable complex with proteins.

EXAMPLE 3

Proof of Principle for Size Exclusion

In a next step an alternative size fractionation approach has been used. To this end, size exclusion chromatography (Kristensen et al., *Nat. Methods* 9, 907-909 (2012); Olinares et al., *Mol. Cell. Proteomics* 9, 1594-1615 (2010)) has been applied to the native protein-metabolite extract using a column which separates molecular complexes from approximately 600 kDa to 10 kDa (FIG. 1). The chromatogram of the absorption at 280 nm indicates reproducible separation of complexes by SEC (FIG. 3a). The protein content in the collected fractions showed separation of protein containing molecular complexes, whereas no protein was detectable in fractions later than C12 corresponding to a molecular mass smaller than 10 kDa (FIG. 3a-b).

EXAMPLE 4

Analysis of Ligands Found in Either Approach

In order to see whether or not the protein fractions contained metabolites/small molecules, 57 fractions for occurrence of semi-polar metabolites were analyzed by LC/MS. According to the results obtained from size filtration we detected the majority of metabolic features, i.e. ligands, as non-protein bound and therefore eluting after one total mobile phase volume of the column (FIG. 3c). In addition and more important, however, we detected specific elution profiles of small molecules in fractions representing theoretical MWs between 10 to 600 kDa.

Three features of small molecule elution profiles are worth commenting. Firstly, the SEC results confirmed to a large extent the results of the size filtration experiment described above. Thus 83 of the putatively annotated protein-interactors, i.e. ligands, from the size filtration experiment were also observed in the SEC data distributed along the whole separation range (FIG. 3d). Secondly, for most metabolites/ligands we observed their occurrence in specific fractions of the SEC experiment and not throughout all fractions which is a clear indication of a specific binding to one or more proteins eluting in these fractions. Thirdly and most important for proof of concept, we observed well-known metabolites interacting with proteins most notably co-factors such as FMN or NAD to display distinct peaks in the separation range indicating the presence of multiple though specific binding to protein(s) (FIG. 3e-f).

To assure that differential eluting metabolites are truly metabolite-protein complex derived, we performed a control experiment with a protein-free sample. To this end, we precipitated proteins from the input sample with 80% acetone and reconstituted the small molecules in lysis buffer before applying it to the SEC column. In line with SEC separating molecular complexes based on their size we did not observe any significant differential metabolic features across the SEC fractions (FIG. 3c) but all metabolites appeared after the total mobile phase volume as expected for free small molecules.

EXAMPLE 5

Co-Fractionation Analysis

Co-fractionation analysis of small molecules and macromolecules (proteins) has been performed. FIG. 4(a) shows a hierarchical cluster dendrogram of proteins and putatively annotated small molecules based on Pearson correlation. Grey boxes indicate clusters that have a correlation coefficient greater than 0.7. FIG. 4(b) shows cluster no 5 from (a) as network where edge weights correspond to correlation strength. FIG. 4(c) shows individual two dimensional plots of elution profiles from selected small molecules (solid lines) and two proteins (dashed lines) with highly similar profiles. Correlation plots are shown in insets.

EXAMPLE 6

Identification of a Novel Gly-Pro: RBA6 Interaction

We demonstrated that by applying any kind of size separation to a native biological lysate, it is possible to separate free small molecules from those bound to the protein complexes. Using single step size filtration we found evidence for multiple dipeptides being bound to the proteins from the soluble fraction isolated from an Arabidopsis cell culture. The follow up experiments, in which protein-small molecule complexes were separated by size exclusion chromatography, demonstrated that dipeptides not only bind to proteins but to specific protein complexes. The majority of the measured dipeptides had one specific elution peak. We focused on one of the measured dipeptides, namely Gly-Pro, that eluted together with protein complex of approximately 145-165 kDa (FIG. 5).

L-Gly-L-Pro was immobilised on the agarose beads either using N terminal group of glycine or C terminal group of proline, referred to as N or C beads. Both resins were incubated with the native Arabidopsis lysate and proteins captured on the beads were eluated with high concentration of Gly-Pro. Affinity experiments suffer from a high rate of false positives related to the unspecific binding. To counteract this and prior to Gly-Pro elution we introduced an extra step where beads were incubated with a mix of glycine and proline. This extra step reduced the number of hits from hundreds to 34 proteins pulled with N and C beads. These include the cytoplasmic fructose bisphosphate aldolases (FBA8 and FBA8) (FIG. 5). They also co-elute with Gly-Pro in the SEC experiment (FIG. 5). Aldolases are enzymes in the glycolysis and gluconeogenesis pathway. They catalyse the reversible reaction in which fructose 1,6 bisphosphate (Fru1,6bP) is cleaved into two three carbon products, namely 3-phosphate glyceraldehyde (G3P) and dihydroxyacetone phosphate (DHAP).

We could subsequently confirm the Gly-Pro: FBA6 interaction by independent methods, both in the cellular extract and in vitro.

We reasoned that if FBA6 can be pulled using Gly-Pro as a bait, the reverse will also be true. To test this assumption, transgenic lines expressing FBA6 together with an affinity tag were prepared, and used in the pull-down experiment. As expected, Gly-Pro was found in the complex with the tagged FBA6 (FIG. 6).

FBA6 protein was expressed and purified from E. coli. MST uses the intristic tendency of all the biological molecules to move in the temperature gradient. This movement is dependent on the molecule size, charge and hydration shell. Complex formation affects at least one of the three parameters changing the movement and indicating binding event. Gly-Pro, but not Pro-Gly, binds FBA6 with the Kd of approximately 200 nM, which is comparable to the substrate (DHAP). The results obtained point to both strong and specific interaction.

EXAMPLE 7

In the course of analyzing co-eluting proteins and metabolites from the SEC experiment, we looked for those which are present in the same metabolic pathway, given that this may indicate feedback regulation.

Two examples could be confirmed:
Pantothenic acid co-eluated with 3-methyl-2 oxobutanoate hydroxymethyl-transferase 1, an enzyme up-stream of the pantothenic acid synthesis (FIG. 8).
Methylthioadenosine co-eluated with Methylthioribose-1-phosphate isomerase (MTR-1-P), an enzyme of the methionine salvage pathway (FIG. 9).

EXAMPLE 8

Identification and Characterization of the cAMP-Rbp47b Interaction
Introduction

Protein-metabolite interactions (PMIs) are essential in all aspects of cell regulation. Recently, to identify potential regulatory small molecules on account of their presence in stable complexes with proteins, we developed a simple approach based on co-fractionation that exploits size differences between protein-metabolite complexes and free metabolites (Veyel et al. (2017) System-wide detection of protein-small molecule complexes suggests extensive metabolite regulation in plants. Sci Rep 7: 42387).

Applying state-of-the-art metabolomic analysis (Giavalisco et al. (2011) Elemental formula annotation of polar and lipophilic metabolites using (13) C, (15) N and (34) S isotope labeling, in combination with high-resolution mass spectrometry. Plant J 68: 364-376.) we identified a multitude of protein-bound small molecules, suggesting the existence of numerous novel small-molecule regulators in Arabidopsis cells. Among the metabolites co-fractionating with proteins we could identify 2',3'-cAMP. In contrast to its positional isomer 3',5'-cAMP, a well-known secondary messenger, the biological function of 2',3'-cAMP is far from fully understood. In fact it was only in 2009 that (Ren et al. (2009) Identification and quantification of 2',3'-cAMP release by the kidney. J Pharmacol Exp Ther 328: 855-865.) reported the existence of 2',3'-cAMP in biological material. Since then 2',3'-cAMP was detected in both mammalian and plant cells, its levels corresponding to stress and injury (Van Damme et al. (2014) Wounding stress causes rapid increase in concentration of the naturally occurring 2',3'-isomers of cyclic guanosine- and cyclic adenosine monophosphate (cGMP and cAMP) in plant tissues. Phytochemistry 103: 59-66; Jackson et al. (2009) Extracellular 2',3'-cAMP is a source of adenosine. J Biol Chem 284: 33097-33106; Verrier et al. (2012) The brain in vivo expresses the 2',3'-cAMP-adenosine pathway. J Neurochem 122: 115-125). 2',3'-cAMP is formed during mRNA degradation, when hydrolysis of the P—O5' bond mediated by RNases is accompanied by transphosphorylation of mRNA to form 2',3'-cyclic nucleotides (Thompson et al. (1994) Energetics of catalysis by ribonucleases: fate of the 2',3'-cyclic phosphodiester intermediate. Biochemistry 33: 7408-7414). Because of the mRNAs poly-A tail, 2',3' cAMP is the most abundant of all the 2',3'-cyclic nucleotides. Similar to its metabolism, also the role of 2',3'-cAMP is not well understood. In rat brain mitochondria, 2',3'-cAMP, was shown to activate mitochondrial transition pores (Azarashvili et al. (2009) Ca2+-dependent permeability transition regulation in rat brain mitochondria by 2',3'-cyclic nucleotides and 2',3'-cyclic nucleotide 3'-phosphodiesterase. Am J Physiol Cell Physiol 296: C1428-1439.), leading to apoptosis and necrosis. To counteract this effect it is suggested that cells export 2',3'-cAMP to the extracellular compartment, where it is metabolized to 2'-AMP and adenosine (Jackson et al. (2009) (loc. cit.); Jackson (2016) Discovery and Roles of 2',3'-cAMP in Biological Systems. Handb Exp Pharmacol.). Intrigued by our observation that 2',3'-cAMP co-migrates with proteins (Veyel (2017) (loc. cit.)), we questioned whether or not 2',3'-cAMP might serve as more than a mere intermediate in the extracellular 2',3'-cAMP adenosine salvage pathway.

Herein, we show that 2',3'-cAMP forms a complex with the Rbp47b protein in vitro and in the native cellular lysate. The Rbp47b protein and its mammalian homolog TIA1 are well recognized as part of the RNA processing machinery (Kedersha et al. (1999) RNA-binding proteins TIA-1 and TIAR link the phosphorylation of eIF-2 alpha to the assembly of mammalian stress granules. Journal of Cell Biology 147: 1431-1441; Gilks et al. (2004) Stress granule assembly is mediated by prion-like aggregation of TIA-1. Mol Biol Cell 15: 5383-5398). Under non-stressed conditions Rbp47b/TIA1 localizes to the nucleus, acting as a component of the pre-mRNA splicing machinery (Gilks (2004) (loc. cit.); Lorkovic et al. (2000) RBP45 and RBP47, two oligouridylate-specific hnRNP-like proteins interacting with poly(A)+ RNA in nuclei of plant cells. RNA 6: 1610-1624). Upon stress Rbp47b/TIA1 re-localizes to the cytoplasm, where its aggregation marks the formation of stress granules (Kedersha (1999) (loc. cit.); Weber et al. (2008) Plant stress granules and mRNA processing bodies are distinct from heat stress granules. Plant J 56: 517-530). SGs are mRNP particles composed of large aggregates of stalled translation pre-initiation complexes, which contain mRNA, 40S ribosomal subunits, translation initiation factors and RNA-binding proteins (RBPs) (SGs) (Kedersha (1999) (loc. cit.), Weber (2008) (loc. cit.); Kedersha et al. (2005) Stress granules and processing bodies are dynamically linked sites of mRNP remodeling. J Cell Biol 169:871-884; Anderson and Kedersha (2009) RNA granules: post-transcriptional and epigenetic modulators of gene expression. Nat Rev Mol Cell Biol 10: 430-436; von Roretz et al. (2011) Turnover of AU-rich-containing mRNAs during stress: a matter of survival. Wiley Interdiscip Rev RNA 2: 336-347; Mahboubi and Stochaj (2017) Cytoplasmic stress granules: Dynamic modulators of cell signaling and disease. Biochim Biophys Acta 1863: 884-895). Process of SGs formation is essential for cell survival due to its involvement in the translation repression. In essence, SGs sequester housekeeping mRNAs and apoptosis regulatory factors, whilst exclude mRNAs encoding proteins involved in stress tolerance. Defects in SG assembly and disassembly can contribute to neurodegeneration (Wolozin (2012) Regulated protein aggregation: stress granules and neurodegeneration. Mol Neurodegener 7: 56).

SG assembly is also a target in cancer research, as presence of SG in cancer cells makes them more resistant to treatment and prone to metastasis (Mahboubi and Stochaj (2017) (loc. cit.)). In contrast, SG integrity is important for viral resistance, by confining viral RNA and proteins (Yoneyama et al. (2016) Regulation of antiviral innate immune signaling by stress-induced RNA granules. J Biochem 159: 279-286).

Having such a key importance for human health, stress granules assembly and disassembly attracted much attention in the past, and is still very much debated (Anderson and Kedersha (2008) Stress granules: the Tao of RNA triage. Trends Biochem Sci 33:141-150; Wheeler et al. (2016) Distinct stages in stress granule assembly and disassembly. Elife 5). Known events include phosphorylation of the translation initiation factor eIF2 that impedes association of tRNA$^{Met}$ to the 43S pre-initiation complex, and thus leads to the translational repression. Rather than undergoing translation mRNA molecules of the 43S complex associate with the RNA-binding proteins, such as Rbp47b and TIA1, which support protein aggregation and
stress granule formation. The self-assembly of the Rbp47b/TIA1 proteins depends on RRM RNA binding motives, known to recruit mRNAs, and on the prion-like PRD domain that supports protein-protein interactions (Gilks (2004) (loc. cit.); Weber (2008) (loc. cit.)). In line with its granule-nucleating activity, the overexpression of TIA-1 induces SG assembly, even in the absence of stress (Gilks (2004) (loc. cit.)).

Post-translational modifications (PTMs) of SG proteins can affect granule dynamics. For example oxidation of TIA1 protein inhibits SG formation sensitizing cells to apoptosis (Arimoto-Matsuzaki et al. (2016) TIA1 oxidation inhibits stress granule assembly and sensitizes cells to stress-induced apoptosis. Nat Commun 7: 10252).

Our research indicates that in addition to PTMs, SG assembly can be directly regulated by small molecule regulator, as 2',3'-cAMP, not only binds to Rbp47b/TIA1 but also promotes its oligomerization. In that way, our research is important for number of reasons. First, we assign an important regulatory function to a novel small molecule, which to date has been only discussed as a by-product of RNA degradation. Second, we provide evidence for the existence of small molecule regulation during stress granule formation, a process of pivotal importance during stress response. Third, our findings point to a mechanism conserved among eukaryotic cells suggesting evolutionary importance.

Results
Identification of the 2',3'-cAMP Protein Receptor in the Native Cellular Extract To this end we set out to identify the binding protein partners of 2',3'-cAMP by applying affinity purification (AP) using agarose beads, with 2',3'-cAMP linked via the NH2 group of the purine ring. After incubation of the beads with total soluble-protein extracts from *A. thaliana* cell suspension cultures (cf. Materials and Methods) sequential washings with ADP, GDP, 5'-AMP, and finally 2',3'-cAMP were performed, and the proteins eluting in the different washings were analyzed by LC-MS/MS proteomics. Proteins eluting from the agarose beads exclusively with 2',3'-cAMP but absent in any of the other eluents (ADP, GDP, or 5'-AMP; FIG. 10A) were defined as 2',3'-cAMP-binding. Applying this stringent criterion only one protein remained: the polyadenylate-binding protein Rbp47b. We reasoned that the putative formation of Rbp47b-2',3'-cAMP complexes in vivo should be reflected by largely overlapping elution profiles of the two components in a size-exclusion experiment (SEC), as was indeed the case (FIG. 10B). To obtain further and independent evidence for the formation of a complex between Rbp47b and 2',3'-cAMP, we performed a cellular thermal shift assay (CETSA) (Franken et al. (2015) Thermal proteome profiling for unbiased identification of direct and indirect drug targets using multiplexed quantitative mass spectrometry. Nat Protoc 10: 1567-1593). CESTA is a method used in the drug research to verify ligand-receptor binding in the native cellular lysate, based on the observation that presence of the ligand changes thermal stability of the protein receptor. Herein, we adapted the protocol to be suitable for the plant material and an endogenous 98 metabolite. We used Arabidopsis cells expressing a tagged version of the Rbp47b, so that Rbp47b level could be easily detected with the anti-tag antibody. Incubation of the native protein lysates with 10 and 100 μM 2',3'-cAMP resulted in thermal destabilization of the Rbp47b protein and change of its melting temperature by 2.4° C. and 5.1° C., respectively, suggesting that 2',3'-cAMP indeed binds to Rbp47b (FIG. 10C). No such effect was observed in an analogous experiment in which the positional isomer 3',5'-cAMP rather than 2',3'-cAMP was used. Taken together, three independent experimental approaches (AP, SEC, and CETSA) provide evidence for the binding of 2',3'-cAMP to Rbp47b in the native Arabidopsis lysate.

In Vitro Confirmation of the 2'3'-cAMP-Rbp47b Interaction

Although the results of the affinity purification suggest a specific binding of 2',3'-cAMP to Rbp47b, no definite conclusion could be drawn regarding the binding affinity and hence the supposed binding specificity. We therefore attempted to determine the in vitro binding affinity biophysically using micro-scale thermophoresis (MST) (Jerabek-Willemsen et al. (2011) Molecular interaction studies using microscale thermophoresis. Assay Drug Dev Technol 9: 342-353). MST exploits the effect of size, charge, and hydration shell on the movement of molecules in a temperature gradient. Complex formation resulting in alteration of at least one of the three parameters leads to differential movement, from which the binding affinity can be determined. For the purpose of the MST experiment, Rbp47b was expressed in and purified from *E. coli*. The MST results show clear binding, with a Kd value of 1 μM. Most importantly we did not observe any binding for 3',5'-cAMP, indicating very high specificity of Rb47b for 2',3'-cAMP (FIG. 11A). The measured Kd value also corresponds to the ~20 μM concentration of 2',3'-cAMP measured in the native Arabidopsis lysate (FIG. 11B).

Biological Significance of Rbp47b-2',3'-cAMP Interaction

In plants 2',3'-cAMP levels increase rapidly under wounding stress (Van Damme (2014) (loc. cit.)). To test whether 2',3'-cAMP level changes in other stress conditions we queried metabolomics date from stress time-course of (Caldana et al. (2011) High-density kinetic analysis of the metabolomic and transcriptomic response of Arabidopsis to eight environmental conditions. Plant J 67: 869-884). Shortly, mature Col-0 rosettes (prior bolting) grown in the control environment, were transferred into combinations of light (low light, high light, darkness) and temperature stress conditions (heat and cold) and sampled in multiple time-points until 24 h following stress onset. 2',3'-cAMP accumulates in low light and darkness, but most notably under heat stress (FIG. 12A), conditions characterized by increased RNA degradation (Merret et al. (2013) XRN4 and LARP1 are required for a heat-triggered mRNA decay pathway involved in plant acclimation and survival during thermal stress. Cell Rep 5: 1279-1293; Baginsky and Gruissem (2002) Endonucleolytic activation directs dark-induced chloroplast mRNA degradation. Nucleic Acids Res 30: 4527-4533) and formation of the stress granules (SGs) (Kedersha (1999) (loc. cit.); Weber (2008) (loc. cit.)). In line, with the rapid accumulation of 2',3'-cAMP levels upon heat stress (within first 20 min, FIG. 12A), Gutierrez-Beltran et al. (2015) (Tudor staphylococcal nuclease links formation of stress granules and processing bodies with mRNA catabolism in Arabidopsis. Plant Cell 27: 926-943) showed that stress granules containing RFP-Rbp47b are formed with in the first 30 minutes of heat stress. If the interaction takes place in the cytosol, where both, Rbp47b and 2',3'-cAMP are present, one would expect that 2',3'-cAMP might influence stress granules formation, meaning oligomerization of Rbp47b. Due to the lack of commercially available membrane permeable derivative of 2',3'-cAMP molecule, we were unable to follow stress granules formation in vivo. However we tested this hypothesis directly by determining the oligomerization of Rbp47b in the presence and absence of saturating amounts of 2',3'-cAMP by MST. As shown in FIG. 12B, Rbp47b self-assembly occurred in the absence of 2',3'-cAMP with a Kd value of 128 nM. Remarkably, a significant shift in the oligomerization affinity-constant was observed in the presence of saturating amounts (50 µM) of 2',3'-cAMP, featuring a Kd value of 9 nM (FIG. 12B). These data strongly suggest that 2',3'-cAMP, as a result of its binding to Rbp47b, exerts direct influence on the oligomerization of this protein, and thus likely on the SG assembly process which requires Rbp47b oligomerization. 2',3'-cAMP, besides being the degradation product of mRNA, could play a regulatory role by influencing the oligomerization of the Rbp47b protein, in turn influencing the formation of SGs.

Evolutionary Conservation of Rbp47b-2',3'-cAMP Interaction

Expecting such a basic role of 2',3'-cAMP to be conserved, we performed similar analysis with TIA1, the human functional homolog of Rbp47b. TIA1 was labeled and its interaction with 2',3'-cAMP was determined using MST. In line with the Rbp47b results, recombinant TIA1 formed a complex with 2',3'-cAMP (Kd=217 µM) but not with 3',5'-cAMP (FIG. 13A). Most importantly, here too 2',3'-cAMP lowered the Kd for TIA1 self-assembly, this time by a factor of 2 (from Kd=36 nM to Kd=20 nM in the presence of 500 µM 2',3'-cAMP; FIG. 13B), demonstrating a remarkably conserved mechanism.

Discussion

2',3'-cAMP a Novel Regulator of Stress Granules (SGs) Assembly

The main finding of herein presented research is specific and high-affinity binding of 2',3'-cAMP to the Arabidopsis Rbp47b protein, and its animal homologue TIA1 protein. A Kd value of 1 µM, measured for the Rbp47b-2',3'-cAMP interaction is within the binding affinity range reported for various receptor-ligand interactions, such as between the gibberellin receptor GID1 and 16,17-dihydro-GA4 (Kd=1.4 µM), and between abscisic acid and PYR1 receptor (Kd=97 µM) (Ueguchi-Tanaka et al. (2005) GIBBERELLIN INSENSITIVE DWARF1 encodes a soluble receptor for gibberellin. Nature 437: 693-698; Dupeux et al. (2011) A thermodynamic switch modulates abscisic acid receptor sensitivity. EMBO J 30: 4171-4184). In that way, and firstly we assigned an important regulatory function to a novel small molecule, which to date has been only discussed as a by product of RNA degradation (Thompson (1994) (loc. cit.)). In cells mRNA decay is associated with cytoplasmic mRNP foci, referred to as processing bodies (P bodies, PBs). RNA decay related to stalled translation is induced under stress conditions in both animals and in plants, e.g. (Merret (2013) (loc. cit.); Heikkinen et al. (2003) Initiation-mediated mRNA decay in yeast affects heat-shock mRNAs, and works through decapping and 5'-to-3' hydrolysis. Nucleic Acids Res 31: 4006-4016; Soma F, Mogami J, Yoshida T, Abekura M, Takahashi F, et al. (2017) ABA-unresponsive SnRK2 protein kinases regulate mRNA decay under osmotic stress in plants. Nat Plants 3: 16204). This is accompanied by an increased number and size of PBs (Sheth and Parker (2003) Decapping and decay of messenger RNA occur in cytoplasmic processing bodies. Science 300: 805-808; Xu et al. (2006) Arabidopsis DCP2, DCP1, and VARICOSE form a decapping complex required for postembryonic development. Plant Cell 18: 3386-3398). Also 2',3'cAMP levels increase under stress and injury e.g. van Damme (2014) (loc. cit.), which fits with the speculated origin of the 2',3'-cyclic nucleotides. We could show that heat treatment leads to the 2',3'-cAMP accumulation within the first 30 min following stress onset. This time-line coincides with the heat triggered formation of stress granules (SGs) (Kedersha (1999) (loc. cit.); Weber (2008) (loc. cit.)), cytoplasmic mRNP foci playing a role in translational repression, by selective stabilization and storage of the mRNAs (Kedersha (1999) (loc. cit.); Weber (2008) (loc. cit.); Kedersha (2005) (loc. cit.); Anderson (2009) (loc. cit.)).

Rbp47b/TIA1 aggregation is a key even is SG formation and we could further demonstrate that the self-assembly is facilitated by 2',3'-cAMP binding. In that way and secondly, we provide evidence for the existence of small molecules regulation during stress granule formation, in addition to already reported PTMs of SGs proteins e.g. Arimoto-Matsuzaki (2016) (loc. cit.). An RNA degradation product, 2',3'-cAMP is highly suitable for such a role, providing a means of negative-feedback regulation between RNA degradation and storage. We speculate that under control conditions nuclear localization of Rbp47b/TIA1 prevents the interaction from taking place. Under stress conditions, often accompanied by rapid increase in 2',3'-cAMP levels, Rbp47b/TIA1 migrates to the cytoplasm, where the interaction can take place, promoting SG formation. Concluding, our results suggest that in both humans and plants 2',3'-cAMP might be a key regulator of the balance between degradation and storage of RNA.

Size Exclusion Chromatography as a Starting Point for the Receptor Studies

Small-molecule target identification is a vital but still formidable task for the chemical biology community. Recently, we proposed size filtration as an effective approach for the global identification of small molecules bound to protein complexes in a native cellular extract. As such this approach allows for rapid screening of multiple biological samples to find conditions in which molecule of choice is present in a protein complex. When followed by size exclusion chromatography (SEC), identity of the protein receptor may be inferred from the co-elution profile. This study constitutes a proof of concept for our approach. We selected 2',3'-cAMP molecule based on its presence in protein complexes from Arabidopsis cell cultures in both simple size filtration and SEC experiments. 2',3'-cAMP co-eluted with several hundreds of proteins (data not shown), and thus to restrict number of candidate protein partners, we followed with the affinity chromatography. Overlay of the two approaches resulted in one candidate protein, which bound specifically to the 2',3'-cAMP resin and co-eluted with 2',3'-cAMP in the SEC experiment. Rbp47b-2',3'-cAMP interaction was than validated by targeted approaches (CETSA and MST). Experimental pipeline presented here has number of advantages (1) it is time (less than a year) and labor effective (2) combines multiple line of evidence (3) combines in situ (cellular extract) and in vitro approaches.

Materials and Methods

Arabidopsis Cell Cultures

Arabidopsis cells cultures (Menges and Murray (2002) Synchronous Arabidopsis suspension cultures for analysis of cell cycle gene activity. Plant J 30: 203-212) were grown in MSMO medium supplemented with 3% sucrose, 0.05 mg/L kinetin, and 0.5 mg/L 1-naphthaleneacetic acid on an orbital shaker at 130 RPM in the light. Cells were passaged weekly to fresh medium and harvested during logarithmic growth using rapid filtration and liquid-nitrogen snap freezing.

Preparation of Native Arabidopsis Lysate

Plant-cell material was collected as described above and pulverized to homogeneity in liquid nitrogen with mortar and pestle, followed by resuspension in 1 mL lysis buffer (25 mM Tris-HCl, pH 7.5; 0.5 M NaCl; 15 mM MgCl2; 0.5 mM DTT; 1 mM NaF; 1 mM Na3VO4; 1×Protease Inhibitor Cocktail, Sigma-Aldrich P9599, Steinheim, Germany) per 1 g of plant material. Cellular debris was separated by 10 min centrifugation at 4° C., 14,000 RPM. Crude lysate was subjected to ultra-centrifugation (45 min, 4° C., 35,000 RPM) to obtain a soluble fraction referred to as the native Arabidopsis lysate.

Affinity Purification

Custom 2',3'-cAMP agarose beads were purchased from Cube Biotech (Monheim, Germany). 2',3'-cAMP was coupled to the beads using the amine (NH2) group of the purine ring and a 14-carbon spacer arm. Before use, beads were equilibrated with lysis buffer. 3 mL native lysate (approximately 90 mg of total protein) was combined with 150 µL agarose resin (see above), incubated for 1 h on a rotating wheel at 4° C. (binding), transferred to a Mobicol "Classic" (35 µM pore size filter) column and washed with 10 mL wash buffer (0.025 M Tris-HCl, pH 7.5; 0.5 M NaCl). 400 µL 1 mM adenosine diphosphate (Sigma 01905) dissolved in lysis buffer was added to the beads, followed by 1 h incubation at 4° C. in a table shaker (1,000 RPM). Eluate was collected and beads were washed with 10 mL wash buffer. The procedure was repeated using 1 mM guanosine diphosphate (Sigma G7127), 1 mM 5'-adenosine monophosphate (Sigma A2252), and 1 mM 2',3'-cAMP (Sigma A9376). Proteins were precipitated using 2.5 volumes of pre-chilled acetone. Protein pellets were dried in a vacuum concentrator and stored at −20° C.

Size Exclusion Chromatography

Conducted as described in Veyel (2017) (loc. cit.). Shortly, 2.5 mL of soluble fraction corresponding to 50 mg of protein were used for the separations in SEC experiment. Separation was performed using HiLoad 16/600 Superdex 200 prep grade column (GE Healthcare Life Science, Little Chalfont, UK) connected to an ÄKTA explorer 10 (GE Healthcare Life Science, Little Chalfont, UK) operating at 4° C. With the flow rate 0.8 mL/min 57 fractions were collected of which 1 mL was dried in a speed-vac overnight and stored at −80° C. for metabolomic and proteomics analysis. As protein free control experiment, 50 mg of protein of the soluble fraction was precipitated with 80% acetone at −20° C. Denatured proteins were pelleted down by centrifugation and the supernatant was dried overnight in a speed-vac. Small molecules were resuspended the next day in the original volume of lysis buffer and used for size separation.

Proteomics: Sample Preparation and Protein Identification

Conducted as described in Veyel (2017) (loc. cit.).

Cellular Thermal Shift Assay and Western Blot Analysis

TAP-tagged Rbp47b and empty vector lines were prepared as described by (Van Leene et al. (2015) An improved toolbox to unravel the plant cellular machinery by tandem affinity purification of Arabidopsis protein complexes. Nat Protoc 10: 169-187) using the pKCS binary vector and standard Agrobacterium transformation. Native Arabidopsis lysate was incubated with 10 or 100 µM 2',3'-cAMP and with DMSO (used for cAMP solution preparation) as control for 30 min at room temperature with mixing. Further steps were adapted from Franken (2015) (loc. cit.). Shortly, in order to apply a 3-min temperature treatment we used a PCR thermocycler (Eppendorf, Hamburg, Germany) with the following temperatures: 39.9; 41.7; 43.5; 45.8; 48.4; 51.1; 53.8; 56.2; and 59.9° C. Denatured proteins were pelleted by centrifugation (1 min, 14,000 RPM). The remaining soluble proteins were precipitated using 2.5 volumes of pre-chilled acetone. Protein pellets, re-suspended in 6 M urea/2 M thiourea, pH 8, were separated by SDS-PAGE on 10% acrylamide gel, followed by transfer onto a polyvinylidene difluoride membrane (BioRad, München, Germany). Incubations with the peroxidase anti-peroxidase soluble complex antibody (Sigma P1291) and washing steps with Tris-buffered saline/1% Tween-20 were then performed. The SuperSignal™ West Pico Chemiluminescent Substrate (Thermo Fisher 34080, Bremen, Germany) kit was used as a detection system.

Data Analysis of Time-Course Experiment

Heat and darkness Arabidopsis samples are from the time course experiment (Caldana (2011) (loc. cit.)). 2',3'-cAMP was detected using ultra-performance liquid chromatography coupled to an Exactive mass spectrometer (Thermo Fisher) in positive and negative ionization mode as previously described (Giavalisco (2011) (loc. cit.)). Annotation was made allowing 0.1 RT and 5 ppm 265 deviation from the reference compound, supported by fragmentation data.

2',3'-cAMP Absolute Quantification

2',3'-cAMP reference compound (Sigma A9376) was spiked into cellular extract (soluble fraction; see above) in concentrations ranging from 100 µM to 1 mM. To be able to distinguish between endogenous 2',3'-cAMP and the reference compound, lysate was obtained from cells labeled with 15N (Kierszniowska et al. (2009) Ratio-dependent significance thresholds in reciprocal 15N-labeling experiments as a robust tool in detection of candidate proteins responding to biological treatment. Proteomics 9: 1916-1924). Endogenous 2',3'-cAMP was detected with m/z=333.03 (M-H) while the reference compound with m/z=328.05 (M-H), the difference corresponding to five nitrogen atoms. All samples were extracted by a methyl-tert-butyl ether (MTBE)/methanol/water solvent system to separate proteins, lipids, and polar compounds into pellet, organic, and aqueous phases, respectively (Giavalisco (2011) (loc. cit.)). Samples were measured using ultra performance liquid chromatography coupled to an Exactive mass spectrometer (Thermo Fisher) in positive and negative ionization mode as previously described (Giavalisco (2011) (loc. cit.)). Relative intensity measured for increasing concentrations of 2',3'-cAMP standard was used to plot a calibration curve; linear in the 100 nM to 100 μM range.

Source of Recombinant Proteins

TIA1 protein was purchased from Origene (Herford, Germany). Rbp47b was cloned as a C-terminal GFP fusion (to increase protein solubility) into the *E. coli* expression vector pDEST14 containing His6-tag at the N-terminal of the Gateway (Karlsruhe, Germany) cassette. Rosetta cells expressing His6-Rbp47b-GFP were grown at 28° C. overnight and next day were moved to Terrific Broth medium supplied with 1% sucrose and relevant antibiotics. Cultures at OD 0.4 were induced by addition of 0.1 mM IPTG and transferred to 16° C. for overnight incubation.

Next day, cells were disrupted with an Avestin (Mannheim, Germany) EmulsiFlex C3 homogenizer and the protein was purified using imidazole-gradient purification in Ni-NTA agarose (Qiagen 34080, Hilden, Germany). Next we performed size-exclusion chromatography and collected twelve protein fractions. Rbp47b eluted in two fractions, first as $His_6$-Rbp47b-GFP fusion, second as $His_6$-Rbp47b fusion: spontaneous cleavage of the GFP tag is a documented phenomenon (Bird et al. (2015) Green fluorescent protein-based expression screening of membrane proteins in *Escherichia coli*. J Vis Exp: e52357). $His_6$-Rbp47b was used for MST measurements. Protein purity was assessed by SDS-PAGE and protein identification was done using western blot using anti-His6 antibodies.

Micro-Scale Thermophoresis

MST measurements were performed using a Monolith NT.115 instrument (NanoTemper, München, Germany). Capillaries were loaded into the instrument as sets of 13-16 point ligand titrations. Proteins (Rb47b and TIA1) were labeled in phosphate buffer (PBS) using Monolith™ protein labeling kit RED-NHS (amine reactive; MO-L001) according to the manufacturers instruction. Excitation was optimized by varying the LED power to yield emission intensities above 200 AU, corresponding to 10-50 nM labeled protein. Monolith power was set to 60%. Ligands [2',3'-cAMP (Sigma A9376)] and [3',5'-cAMP (Sigma A6885)] were dissolved in PBS. 0.5% Tween and premium coated capillaries were used to prevent sticking. Non-labeled TIA1 and Rbp47b were used as ligands in the self-assembly experiments. MO Affinity Analysis software was used to analyze (Kd calculation) and visualize the data. Presented data are from 2-3 technical replicates.

The invention claimed is:

1. A method of determining ligands of macromolecules in a sample, wherein said sample is a cell-free cell extract, said method comprising or consisting of
    (a) subjecting said sample comprising (i) complexes formed by said macromolecules and said ligands and (ii) unbound ligands, to a method which separates said complexes from said unbound ligands, wherein said method yields fractions and at least two (2) fractions corresponding to a molecular mass of at least about 10 kiloDaltons (kDa) are collected, and wherein said method is size exclusion chromatography (SEC)
    (b) releasing ligands from complexes in each of a plurality of said fractions collected in step (a);
    (c) in each said fraction of step (a) subjected to said releasing step in step (b), subjecting the released ligands obtained in step (b) to a chemical analysis method, thereby determining said ligands in each said fraction; and
    (d) in each said fraction of step (a) subjected to said releasing step in step (b), determining one or more macromolecules in each said fraction by a chemical analysis method;
    wherein said method further comprises
    (e) determining which ligand binds which macromolecule by
        (i) determining the amount of at least one given ligand in each said fraction of step (a) subjected to said releasing in step (b) and said determining in step (c), thereby obtaining an elution profile of said given ligand,
        (ii) determining the amount of at least one macromolecule in each of said fractions of step (a) subjected to said releasing in step (b) and said determining in step (d), thereby obtaining an elution profile of each said macromolecule, and
        (iii) comparing said obtained elution profiles of ligands of step (e)(i) with said obtained elution profiles of macromolecules of step (e)(ii);
    wherein the most likely interaction partner of a said given ligand is the macromolecule having the most similar elution profile to the elution profile of said ligand.

2. The method of claim 1, wherein said ligands comprise at least one of
    (i) ligands which occur naturally in a biological system,
    (ii) ligands having a molecular mass between about 50 Da and 2000 Da, or
    (iii) small organic molecules.

3. The method of claim 1 wherein said macromolecules are at least one of
    (1) proteins, nucleic acids, membranes, or macromolecular assemblies, or
    (2) (i) a proteome or an RNAome, or
        (ii) proteins encoded by a library of nucleic acids, or nucleic acids encoded by a library of nucleic acids.

4. The method of claim 2, wherein said ligands are ligands which occur naturally in a biological system and said macromolecules are a proteome or an RNAome.

5. The method of claim 1, wherein said chemical analysis method of step (c) is at least one of mass spectrometry (MS), nuclear magnetic resonance (NMR), protein sequencing, or detection by antibodies.

6. The method of claim 1, wherein said ligand is a non-covalent ligand.

7. The method of claim 6, wherein said releasing in step (b) is effected by denaturation of said complexes.

8. The method of claim 1, wherein said method further comprises at least one of the following further steps:
    (aa) prior to step (a), breaking up cells comprising said macromolecules and optionally said ligands, followed by removal of insoluble material;
    (ab) after step (a) and prior to step (b), washing;
    (ca) after step (b) and prior to step (c), removing macromolecules, extracting ligands and/or performing liquid chromatography (LC) or gas chromatography (GC) of the ligands, or, if applicable, of the extracted ligands; or
    (da) after step (b) and prior to step (d), to the extent step (d) is performed, extracting macromolecules and optionally performing LC of the extracted macromolecules.

9. A method of identifying, out of a plurality of test compounds, any ligand(s) of one or more macromolecules, said method comprising or consisting of:

(a) bringing said macromolecule(s) into contact with said plurality of test compounds to form a mixture;
(b) subjecting the mixture obtained in step (a) to a method which separates complexes between said macromolecule(s) and ligand(s), if any said complexes have formed, from unbound test compounds, wherein said method yields fractions and at least two (2) fractions corresponding to a molecular mass of at least about 10 kDa are collected, and wherein said method is size exclusion chromatography (SEC);
(c) in each of a plurality of said fractions collected in step (b), dissociating any said complexes, thereby releasing bound ligands, if any, from macromolecules;
(d) in each said fraction of step (b) subjected to said releasing step in step (c), subjecting the released ligand(s) obtained in step (c), if any, to a chemical analysis method, thereby identifying a ligand(s) of said macromolecule(s) wherein said identifying a said ligand comprises identifying a test compound capable of binding to at least one of said macromolecule(s) as a ligand; and
(e) in each said fraction of step (b) subjected to said releasing step in step (c), determining one or more macromolecules in each said fraction by a chemical analysis method;
wherein said method further comprises
(f) determining which test compound capable of binding to at least one of said macromolecule(s) as a ligand binds which macromolecule by
  (i) determining the amount of a given ligand in each of said fractions of step (b) subjected to said releasing step of step (c) and said determining in step (d), thereby obtaining an elution profile of said given ligand,
  (ii) determining the amount of at least one given macromolecule in each of said fractions of step (b) subjected to said releasing step of step (c) and said determining step (e), thereby obtaining an elution profile of each said macromolecule, and
  (iii) comparing said obtained elution profiles of ligands of step (f)(i) with said obtained elution profiles of macromolecules of step (f)(ii);
wherein the most likely interaction partner of a said test compound capable of binding to at least one of said macromolecule(s) as a ligand is the macromolecule having the most similar elution profile to the elution profile of said test compound.

10. The method of claim 9, wherein
(i) said macromolecule(s) comprise at least one of protein(s) or nucleic acid(s); and
(ii) said ligand(s) comprise at least one of
  (aa) ligands which occur naturally in a biological system,
  (bb) ligands having a molecular mass between about 50 Da and 2000 Da, or
  (cc) small organic molecules.

11. The method of claim 9, wherein said chemical analysis method of step (d) is at least one of mass spectrometry (MS) or nuclear magnetic resonance (NMR).

12. A method of identifying druggable macromolecules, said method comprising or consisting of
(a) subjecting a sample comprising
  (i) complexes formed by macromolecules and their ligands, and
  (ii) unbound ligands
to a method which separates said complexes from said unbound ligands, wherein said method yields fractions and at least two (2) fractions corresponding to a molecular mass of at least about 10 kDa are collected, and wherein said method is size exclusion chromatography (SEC);
(b) releasing ligands from said complexes in each of a plurality of said fractions collected in step (a);
(c) in each said fraction of step (a) subjected to said releasing step in step (b), subjecting the released ligands obtained in step (b) to a chemical analysis method, thereby determining said ligands of said macromolecules in said fraction;
(d) in each said fraction of step (a) subjected to said releasing step in step (b), thereby determining one or more said macromolecules in said fraction by a chemical analysis method; and
(e) determining which macromolecule(s), if any, bind a ligand, by
  (i) determining the amount of a given ligand in each said fraction of step (a) subjected to said releasing in step (b) and said determining in step (c), thereby obtaining an elution profile of said given ligand,
  (ii) determining the amount of at least one a given macromolecule in each of said fractions of step (a) subjected to said releasing in step (b) and said determining in step (d), thereby obtaining an elution profile of each said macromolecule, and
  (iii) comparing said obtained elution profiles of ligands with said obtained elution profiles of macromolecules and identifying any said macromolecule having a similar elution profile to the elution profile of a said given ligand, thereby identifying said macromolecule as a molecule binding a ligand;
wherein a macromolecule binding a ligand is a druggable macromolecule.

13. The method of claim 3, wherein said nucleic acids encoded by a library of nucleic acids are RNAs.

14. The method of claim 1, wherein said fractions cover a molecular mass range from about 10 kDa to about 10000 kDa.

15. The method of claim 8, wherein said liquid chromatography (LC) or gas chromatography (GC) of said ligands and/or macromolecules, to the extent it is performed, is effected in at least one of an online LC/MS device, an online LC/NMR device, an online GC/MS device or an online GC/NMR device.

16. The method of claim 10, wherein said ligands which occur naturally in a biological system are at least one of metabolites, peptides, lipids and nucleic acids.

17. The method of claim 2 wherein said ligands which occur naturally in a biological system are at least one of metabolites, peptides, lipids and nucleic acids.

18. The method of claim 17, where ligands are nucleic acids selected from at least one of small RNAs and oligonucleotides.

19. The method of claim 4, wherein said ligands which occur naturally in a biological system are metabolites and said macromolecules are a proteome, thereby obtaining a protein-metabolite interactome.

20. The method of claim 16, wherein said ligands are nucleic acids selected from at least one of RNAs, small RNAs, and oligonucleotides.

* * * * *